(12) United States Patent
Yaffe et al.

(10) Patent No.: US 10,863,989 B2
(45) Date of Patent: Dec. 15, 2020

(54) SURGICAL DEVICES, TECHNIQUES, AND PROCESS FOR LAPAROSCOPICALLY ACCESSING, DISSECTING, RETRACTING OF, AND CUFF PLACEMENT ONTO A SPLENIC ARTERY VIA AN OVER-THE-WIRE APPROACH

(71) Applicant: Verily Life Sciences LLC, South San Francisco, CA (US)

(72) Inventors: Benjamin K. Yaffe, San Francisco, CA (US); Cindy Au, Redwood City, CA (US); Eric Irwin, South San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 143 days.

(21) Appl. No.: 16/230,350

(22) Filed: Dec. 21, 2018

(65) Prior Publication Data
US 2019/0200995 A1 Jul. 4, 2019

Related U.S. Application Data

(60) Provisional application No. 62/615,711, filed on Jan. 10, 2018, provisional application No. 62/611,244, filed on Dec. 28, 2017.

(51) Int. Cl.
*A61B 17/11* (2006.01)
*A61B 17/02* (2006.01)
(Continued)

(52) U.S. Cl.
CPC .......... *A61B 17/11* (2013.01); *A61B 17/0218* (2013.01); *A61B 17/1204* (2013.01);
(Continued)

(58) Field of Classification Search
CPC . A61B 17/11; A61B 17/0218; A61B 17/1204; A61B 17/3423; A61B 17/3474
See application file for complete search history.

(56) References Cited

U.S. PATENT DOCUMENTS 5,158,543 A 10/1992 Lazarus
5,383,889 A 1/1995 Warner et al.
(Continued)

OTHER PUBLICATIONS

International Application No. PCT/US2018/067252, International Preliminary Report on Patentability, dated Jul. 9, 2020, 6 pages.

*Primary Examiner* — Richard G Louis
(74) *Attorney, Agent, or Firm* — Kilpatrick Townsend & Stockton LLP

(57) ABSTRACT

The present disclosure relates to a method for installing a cuff around a target biological structure. The method may include inserting a guidewire through an incision in a patient underneath an exterior surface of a target biological structure, guiding a ramp device over the guidewire to a position underneath the target biological structure such that the target biological structure is partly supported by the ramp device, guiding a cuff deployment tool over the guidewire to the ramp device, the cuff deployment tool comprising an interior volume and a cuff positioned within the interior volume, and causing the cuff from the cuff deployment tool to deploy such that the cuff moves from within the interior volume to an extended position. At least part of the cuff is positioned between the ramp device and the target biological structure in the extended position.

19 Claims, 35 Drawing Sheets

(51) Int. Cl.
  *A61B 17/12* (2006.01)
  *A61B 17/34* (2006.01)
  *A61B 90/00* (2016.01)
  *A61B 17/00* (2006.01)
  *A61B 17/32* (2006.01)
  *A61M 25/01* (2006.01)

(52) U.S. Cl.
  CPC ...... *A61B 17/3423* (2013.01); *A61B 17/3474* (2013.01); *A61B 17/12136* (2013.01); *A61B 17/3421* (2013.01); *A61B 2017/00557* (2013.01); *A61B 2017/00778* (2013.01); *A61B 2017/00946* (2013.01); *A61B 2017/1107* (2013.01); *A61B 2017/12004* (2013.01); *A61B 2017/320048* (2013.01); *A61B 2090/0815* (2016.02); *A61B 2090/0816* (2016.02); *A61M 2025/0175* (2013.01)

(56) References Cited

U.S. PATENT DOCUMENTS

| | | | |
|---|---|---|---|
| 5,439,476 A | 8/1995 | Frantzides | |
| 2004/0199177 A1 | 10/2004 | Kim | |
| 2006/0111626 A1* | 5/2006 | Rossing | A61N 1/05 600/372 |
| 2008/0097497 A1* | 4/2008 | Assad | A61B 17/12 606/157 |
| 2009/0264906 A1* | 10/2009 | McDonnell | A61M 5/427 606/151 |
| 2011/0213408 A1* | 9/2011 | Gross | A61B 5/6862 606/201 |

* cited by examiner

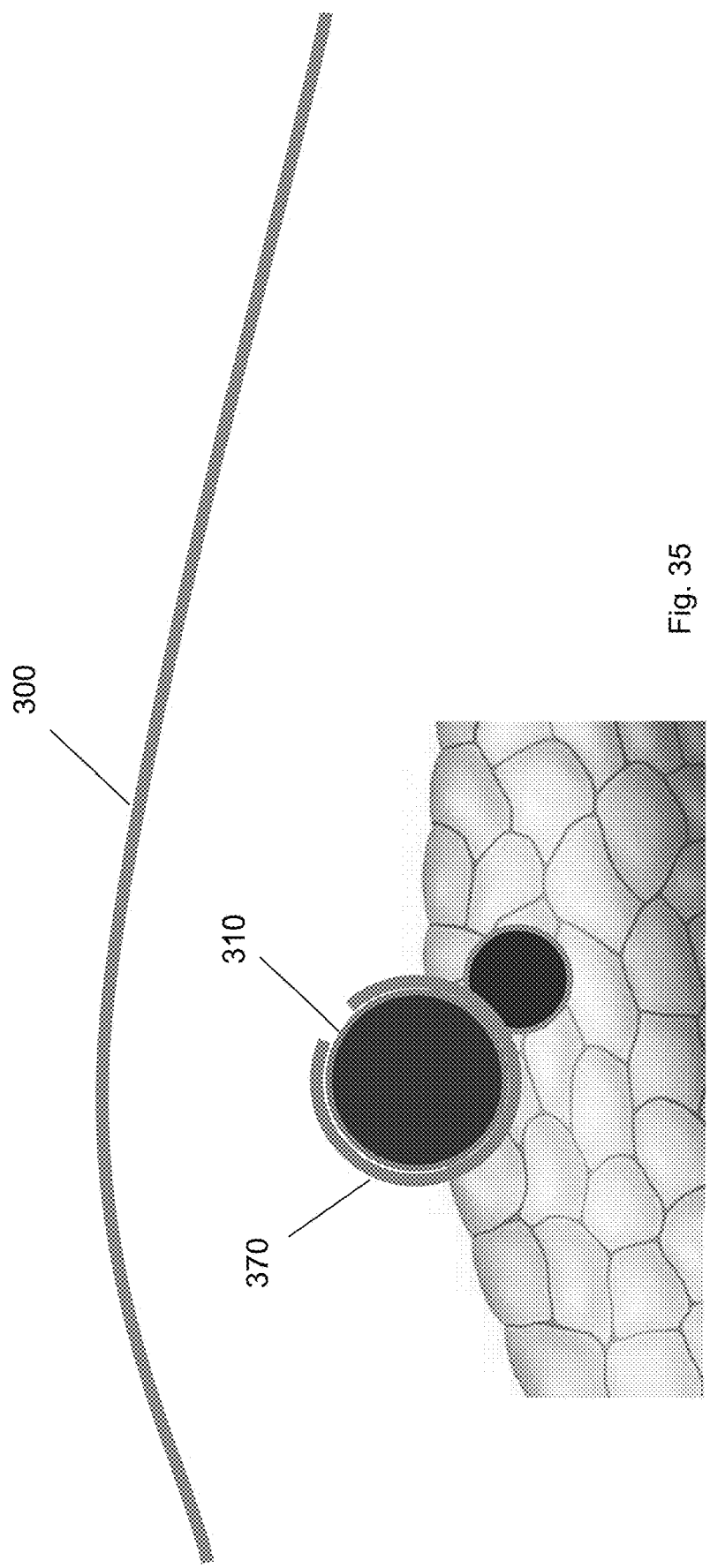

SURGICAL DEVICES, TECHNIQUES, AND PROCESS FOR LAPAROSCOPICALLY ACCESSING, DISSECTING, RETRACTING OF, AND CUFF PLACEMENT ONTO A SPLENIC ARTERY VIA AN OVER-THE-WIRE APPROACH

CROSS-REFERENCE TO RELATED APPLICATION

This application claims the benefit of and the priority to U.S. Provisional Application No. 62/611,244, filed on Dec. 28, 2017, and U.S. Provisional Application No. 62/615,711, filed on Jan. 10, 2018, which are hereby incorporated by reference in its entirety for all purposes.

FIELD OF THE INVENTION

The present disclosure generally relates to devices for partly isolating a target biological structure, and more specifically relates to atraumatic devices and methods for partly isolating and supporting a target biological structure that provides multidirectional access to the target biological structure.

BACKGROUND

Laparoscopic surgery is traditionally conducted through a series of small incisions in a patient, e.g., in the patient's abdomen. In laparoscopic procedures, biological structures, e.g., the splenic artery, are often found next to other vasculature, neural tissue, or organs. Often times, surgeries require modification, ligation, incision, or attachment of tools to one of these biological structures. Currently, these procedures may be performed with balloon dissection tools to separate tissue at natural tissue plane boundaries. The tissues may be retracted by gross retractor tools or by silicone vessel retractors that may cause trauma to the surrounding structures. Therefore, less traumatic devices and techniques are needed for these laparoscopic procedures.

SUMMARY

In some embodiments, the present disclosure relates to device for partly isolating a target biological structure in a patient. The device may include a main body comprising a front face and a rear face, the main body having a proximal end and a distal end. The distal end may be arcuate in a first state and may be substantially planar in a second state. The device may further include one or more balloons disposed on the distal end of the main body. Each of the one or more balloons is deflated in the first state and each of the one or more balloons is inflated in the second state. The distal end of the main body is configured to deform to be substantially planar when each of the one or more balloons are inflated in the second state. In one aspect, the device may further include an additional balloon on the rear face of the main body and the additional balloon may be a hemostatic balloon. In another aspect, the one or more balloons comprise a first balloon on a first side of the main body and a second balloon on a second side of the main body. In the second state, a channel exists between the first balloon and the second balloon. In the second state, the first balloon and the second balloon support a target biological structure above the front face of the main body, and the channel is located below the target biological structure.

In another embodiment, the present disclosure relates to a method. The method may include making an incision in a patient, inserting a device, in a first state, to access the target biological structure in the patient through the incision, positioning the device at least partially beneath a target biological structure in the patient, and transitioning the device from the first state to the second state. The device may include a main body comprising a front face and a rear face, the main body having a proximal end and a distal end. The distal end may be arcuate in a first state and may be substantially planar in a second state. The device may further include one or more balloons disposed on the distal end of the main body. Each of the one or more balloons is deflated in the first state and each of the one or more balloons is inflated in the second state. The distal end of the main body is configured to deform to be substantially planar when each of the one or more balloons are inflated in the second state. In the transitioning step, each of the one or more balloons are at least partly inflated and the target biological structure is at least partly supported by each of the one or more balloons.

In another embodiment, the present disclosure relates to a device for positioning a target biological structure in a patient. The device may include a base plate comprising a front face and a rear face, the base plate having proximal and distal ends. The base plate includes a first sidewall disposed on a first end of the front face and a second sidewall disposed on an opposing second end of the front face. A channel exists between the first sidewall and the second sidewall. The base plate may include an end wall positioned on the distal end of the base plate between the first sidewall and the second sidewall. The end wall is inclined relative to the proximal end of the base plate. In one aspect, the first sidewall, the second sidewall, and the end wall each have a constant height defining an area of the channel, wherein a target biological structure is supported on the first sidewall and the second sidewall. In another aspect, each of the first sidewall and the second sidewall comprises a recess on a portion of a surface of each of the first sidewall and the second sidewall that is opposing the front face of the base plate.

In another embodiment, the present disclosure relates to a method. The method may include making an incision in a patient, inserting a device to access a target biological structure in the patient through the incision, and positioning the device at least partially beneath the target biological structure in the patient. The device may include a base plate comprising a front face and a rear face, the base plate having proximal and distal ends. The base plate includes a first sidewall disposed on a first end of the front face and a second sidewall disposed on an opposing second end of the front face. A channel exists between the first sidewall and the second sidewall. The base plate includes an end wall positioned on the distal end of the base plate between the first sidewall and the second sidewall. The end wall is inclined relative to the proximal end of the base plate. The target biological structure is at least partly supported on the first sidewall and second sidewall above the base plate. In one aspect, the rear face of the base plate may include a conduit configured to receive a guidewire. The step of positioning the device comprises threading the device over the guidewire to the target biological structure.

In yet another embodiment, the present invention relates to a method. The method includes inserting a guidewire through an incision in a patient towards an exterior surface of a target biological structure. After the guidewire is inserted, a ramp device may be guided over the guidewire to a position underneath the target biological structure such that the target biological structure is partly supported by the ramp device. The ramp device may have a curvature with respect to a long axis of the guidewire. After the ramp device is guided, a cuff deployment tool is guided over the guidewire to the ramp device. The cuff deployment tool may comprise an interior volume and a cuff positioned within the interior volume. After the cuff deployment tool is guided over the guidewire to the ramp device, the cuff is deployed from the cuff deployment tool such that the cuff moves from within the interior volume to an extended position. At least part of the cuff is positioned between the ramp device and the biological structure in the extended position.

In another embodiment, a method is provided. The method includes making a first incision and a second incision in the skin of a patient and placing a first trocar in the first incision and a second trocar in the second incision. Then, an area underneath the skin of the patient may be insufflated to access a target biological structure. After insufflation, a guidewire may be guided through the first trocar to a position underneath a target biological structure to the second trocar. The guidewire may have a proximal end and a distal end, wherein the distal end of the guidewire may be secured at the second trocar. After the distal end of the guidewire is secured, a balloon tool is guided over the guidewire to a position underneath the target biological structure. The balloon tool may include a balloon that may be caused to inflate when the balloon tool is at the position underneath the target biological structure to provide pressure to the target biological structure. After the balloon is removed, a ramp device may be guided over the guidewire to a position underneath the target biological structure such that the target biological structure is partly supported by the ramp device. The ramp device may include an end wall having a curvature with respect to a long axis of the guidewire. After the ramp device is guided to the target biological structure, a cuff deployment tool is guided over the guidewire to the ramp device. The cuff deployment tool may comprise an interior volume and a cuff positioned within the interior volume. After the cuff deployment tool is guided over the guidewire to the ramp device, the cuff is deployed from the cuff deployment tool such that the cuff moves from within the interior volume to an extended position. At least part of the cuff is positioned between the ramp device and the biological structure in the extended position.

These illustrative embodiments are mentioned not to limit or define the scope of this disclosure, but rather to provide examples to aid understanding thereof. Illustrative embodiments are discussed in the Detailed Description, which provides further description. Advantages offered by various embodiments may be further understood by examining this specification.

BRIEF DESCRIPTION OF THE DRAWINGS

FIG. 35 shows the target biological structure with the cuff according to one embodiment of the present invention.

DETAILED DESCRIPTION

Figure 1:
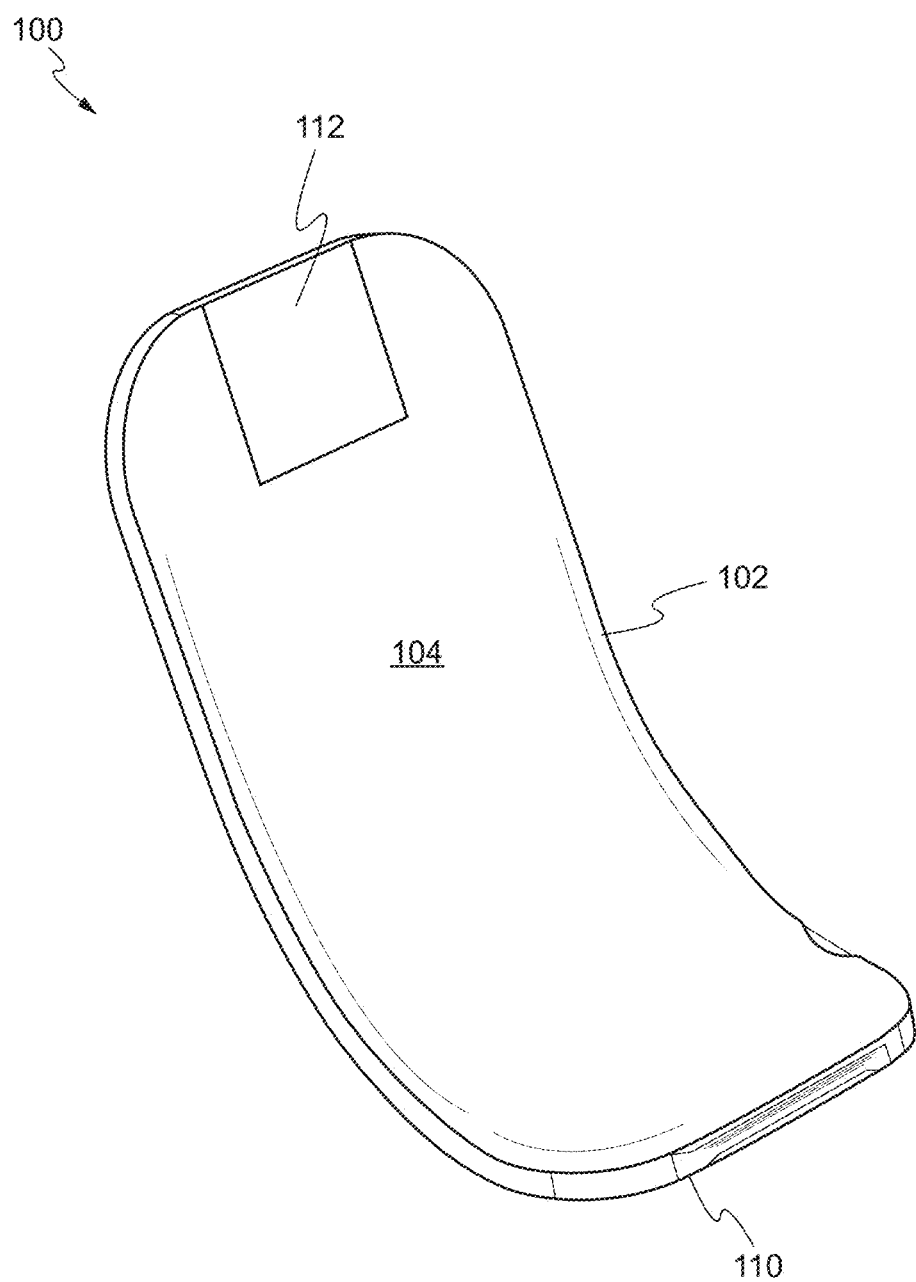
FIG. 1 shows a front perspective view of a device according to one embodiment of the present invention.

Those of ordinary skill in the art will realize that the following description is illustrative only and is not intended to be in any way limiting. Reference will now be made in detail to implementations of embodiments as illustrated in the accompanying drawings. The same reference numerals will be used throughout the drawings and the following description to refer to the same or like items.

The present disclosure relates to devices that allow a user to partly isolate and access a target biological structure in a patient. As used herein, the phrase "target biological structure" refers to any type of vasculature, artery, tissue, or organ. As used herein, the term "patient" refers to any multicellular organism, e.g., an animal (e.g., a human).

In the illustrative embodiments discussed below, the devices may be discussed in the context of positioning an artery from a neurovascular bundle near the pancreas. However, the devices and methods disclosed herein can be used in any laparoscopic procedure. The devices enable a user to partly isolate, i.e., pull away or separate, a target biological structure from surrounding structures, without causing trauma to the surrounding structures or the target biological structure. The device also supports the target biological structure in a manner that provides multidirectional access to areas of the target biological structure.

In some embodiments, the devices may be used during laparoscopic procedures. Laparoscopic surgery may performed through very small incisions in the abdomen of the patient, generally to provide access for a trocar or a cannula device. After incision, the abdomen of a patient may be insufflated with gas in order to expand the abdominal cavity to provide a space to perform laparoscopy. In this example, the devices may be inserted through the small incision to enable a user, e.g., a surgeon, to position and support a target biological structure thereon. While the target biological structure is supported on the device, the user can manipulate, e.g., modify, ligate, incise, or attach tools to, the target biological structure.

Devices

Figure 2:
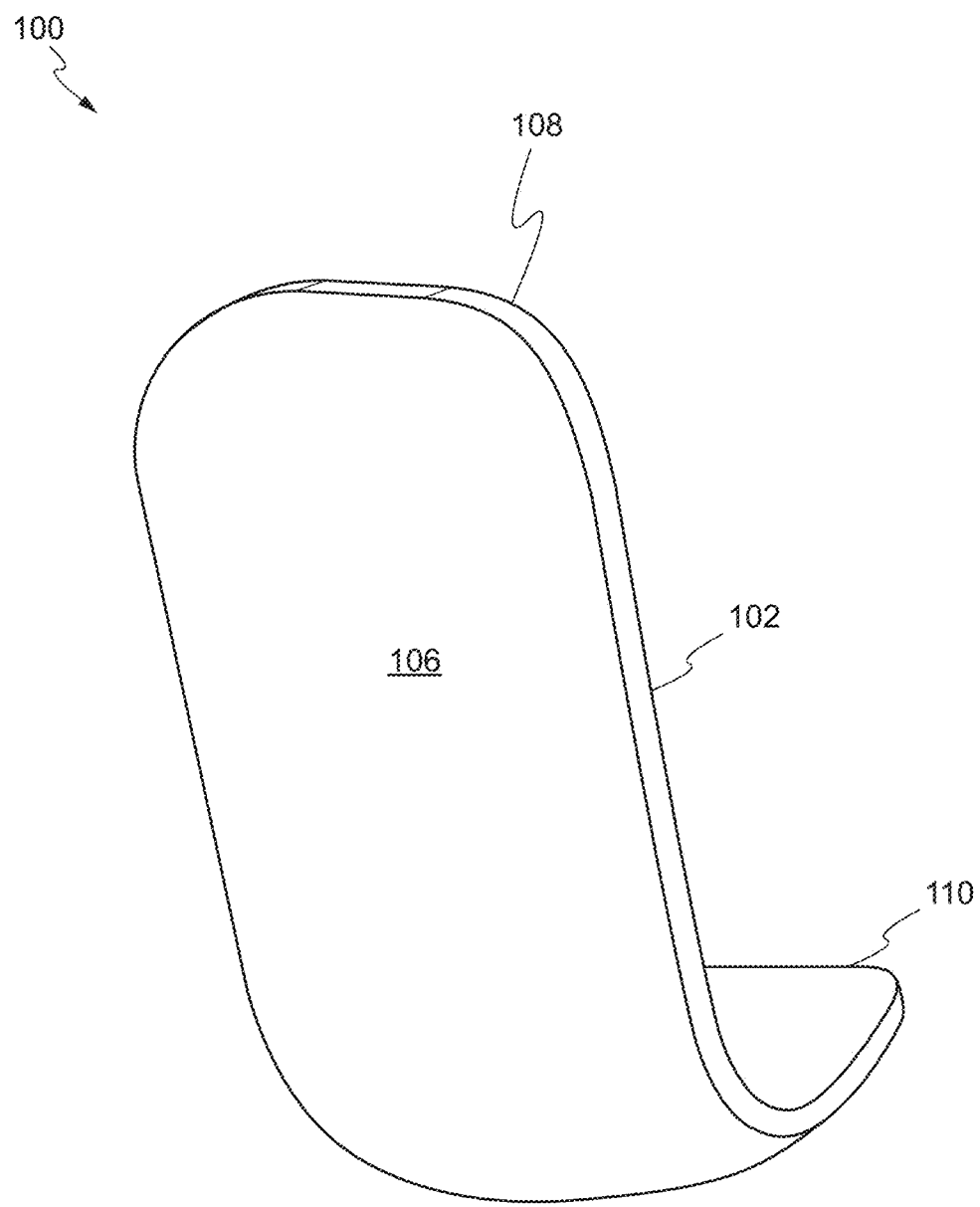
FIG. 2 shows a rear perspective view of the device according to one embodiment of the present invention.

FIGS. 1 and 2 show a front perspective view and a rear perspective view of a device, respectively, according to one embodiment of the present invention. The device 100 may comprise a main body 102 including a front face 104 and a rear face 106. The main body 102 has a proximal end 108 and a distal end 110. The distal end 110 of the main body 102 is substantially arcuate. As used herein, the term "proximal end" refers to a first end of the main body, while the term "distal end" refers to a second end opposing the first end. For example, the proximal end may be an end of the main body which is closest to the user and the distal end may be an end of the main body which is furthest from the user.

The proximal end 108 of the main body 102 is substantially flat and planar with respect to the distal end 110. In some embodiments, the proximal end 108 may include a handle 112. The handle 112 may be removably attached to the proximal end 108. In some embodiments, the handle 112 may be an articulating handle. In use, the user can grasp the handle 112 of the device 100 using hemostatic pliers. In other embodiments, the handle 112 can include a through-hole to thread a suture to function as a retention string. In other embodiments, the handle 112 can be provided on the distal end 110 of the main body 102.

The distal end 110 of the main body 102 is substantially arcuate, i.e., the distal end 110 has a curvature transverse to the longitudinal axis of the proximal end 108. For example, arcuate may refer to the distal end 110 being shaped or bent in the form of an arc or bow with respect to the proximal end 108 of the main body 102. In some embodiments, the distal end 110 may have a constant curvature. In other embodiments, the distal end 110 may have varying degrees of curvature. The distal end 110 enables the device 100 to pull away and isolate the target biological structure from surrounding structures. For example, the distal end 110 can be positioned in a manner to lift and separate the target biological structure from surrounding tissue. In some embodiments, the distal end 110 of the device 100 can be used to separate the splenic artery from a neurovascular bundle adjacent to the pancreas.

In some embodiments, the distal end 110 is deformable, such that the distal end 110 deforms in response to a sufficient force applied to the distal end 110. In particular, the distal end 110 is capable of deforming from an applied force to adjust the curvature of the distal end 110. In this way, the curvature of the distal end 110 can be adjusted for different procedures. Initially, the distal end 110 is arcuate. The distal end 110 of the main body 102 can be sufficiently curved with beveled edges such that it does not cause trauma to surrounding structures. For example, the corners of the distal end are rounded.

The device 100 may be formed of a flexible polymer material, e.g., a thermoplastic polymer. For example, the device 100 can be formed of a firm, lightweight, plastic material such as, polyether ether ketone (PEEK) or polyurethane. The device 100 can also be formed of other flexible medical grade plastic materials. In some embodiments, the device may be formed of a malleable metal, e.g., stainless steel or aluminum. In other embodiments, the device 100 is formed of a rigid material such that it does not substantially deform from an applied force.

In one embodiment, the device 100 can be used for isolating the splenic artery away from the pancreas. In laparoscopic procedures, after the target biological structure, e.g., splenic artery, is separated from the pancreas, there is a space, e.g., about 3 mm to 12 mm, between the target biological structure and the pancreas. When inserting a medical tool in the space between the target biological structure and the pancreas, the medical tool may contact the surrounding biological structures and cause damage. In this respect, the device 100 can operate as a backing plate underneath the target biological structure. This allows the user to exert a force on the device 100 to bias force away from target biological structure or surrounding structures. The device 100 distributes a portion of the force onto the structure below the target biological structure, e.g., the pancreas. After the procedure is over, the device 100 can be withdrawn from the area, such that it is no longer supporting the splenic artery. The device 100 can then be removed from the patient via the incision.

Inflatable Device

Figure 3:
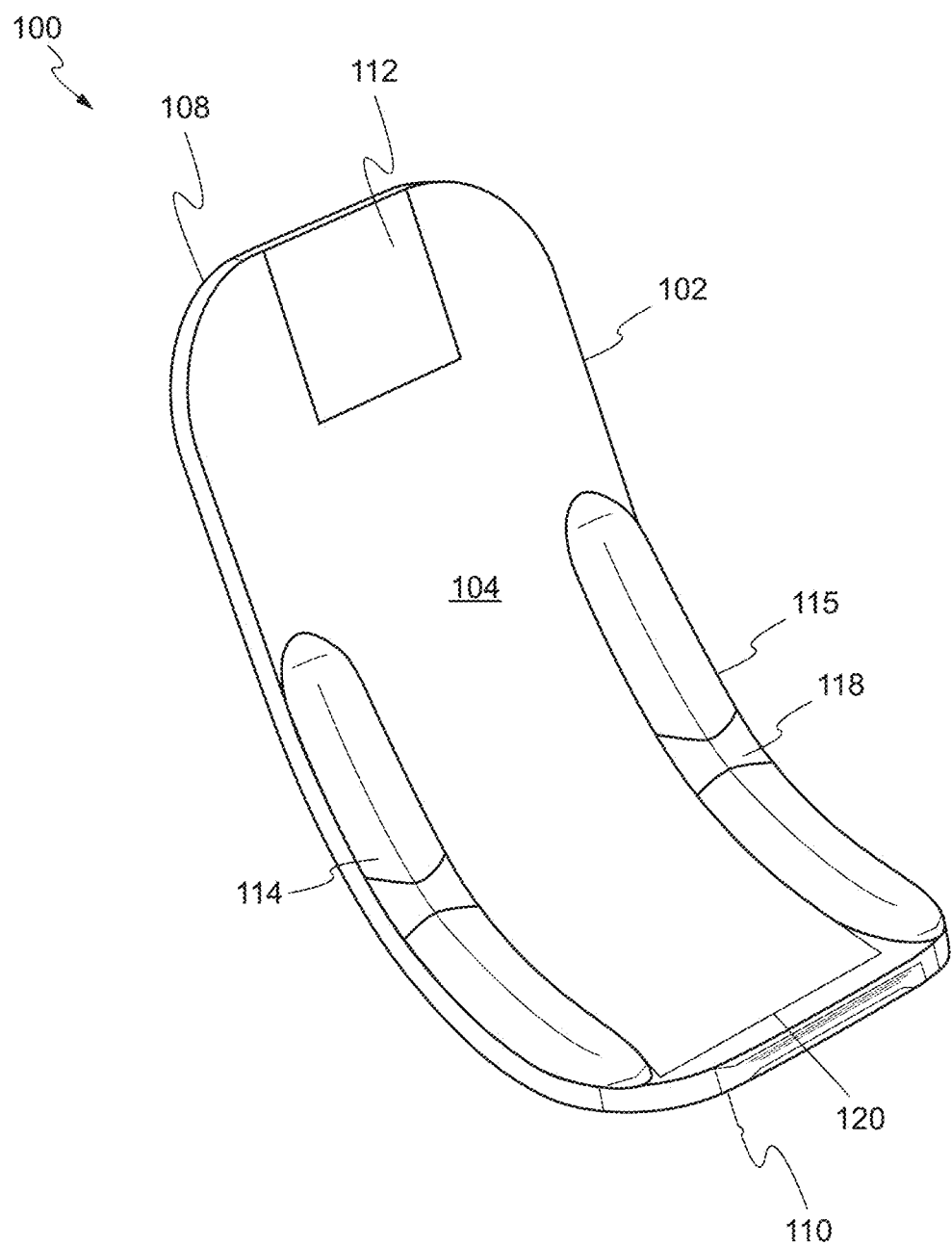
FIG. 3 shows a perspective view of a device, in a first state, according to another embodiment of the present invention.

In another embodiment, the device may include one or more balloons disposed on the main body that are configured to transition the device between a first state and a second state. For example, FIG. 3 shows the device, in a first state, according to one embodiment. In this embodiment, the device 100 isolates and supports a target biological structure away from surrounding structures. As described above, the device 100 may comprise a main body 102 including a front face 104, a rear face 106, a proximal end 108, and a distal end 110.

In this embodiment, the device 100 includes one or more balloons 114, 115 disposed on the distal end 110 of the main body 102. In some embodiments, the one or more balloons 114, 115 are disposed in a position lateral to the main body 102. In a first state, the one or more balloons 114, 115 are deflated. In this configuration, the distal end 110 is substantially arcuate. In some embodiments, each balloon of the one or more balloons 114, 115 includes a recess 118 on a portion of a surface of the balloon that is opposing the front face 104 of the main body 102. The recess 118 provides a space for retaining the target biological structure on the device 100, above the front face 104 of the main body 102.

Figure 4:
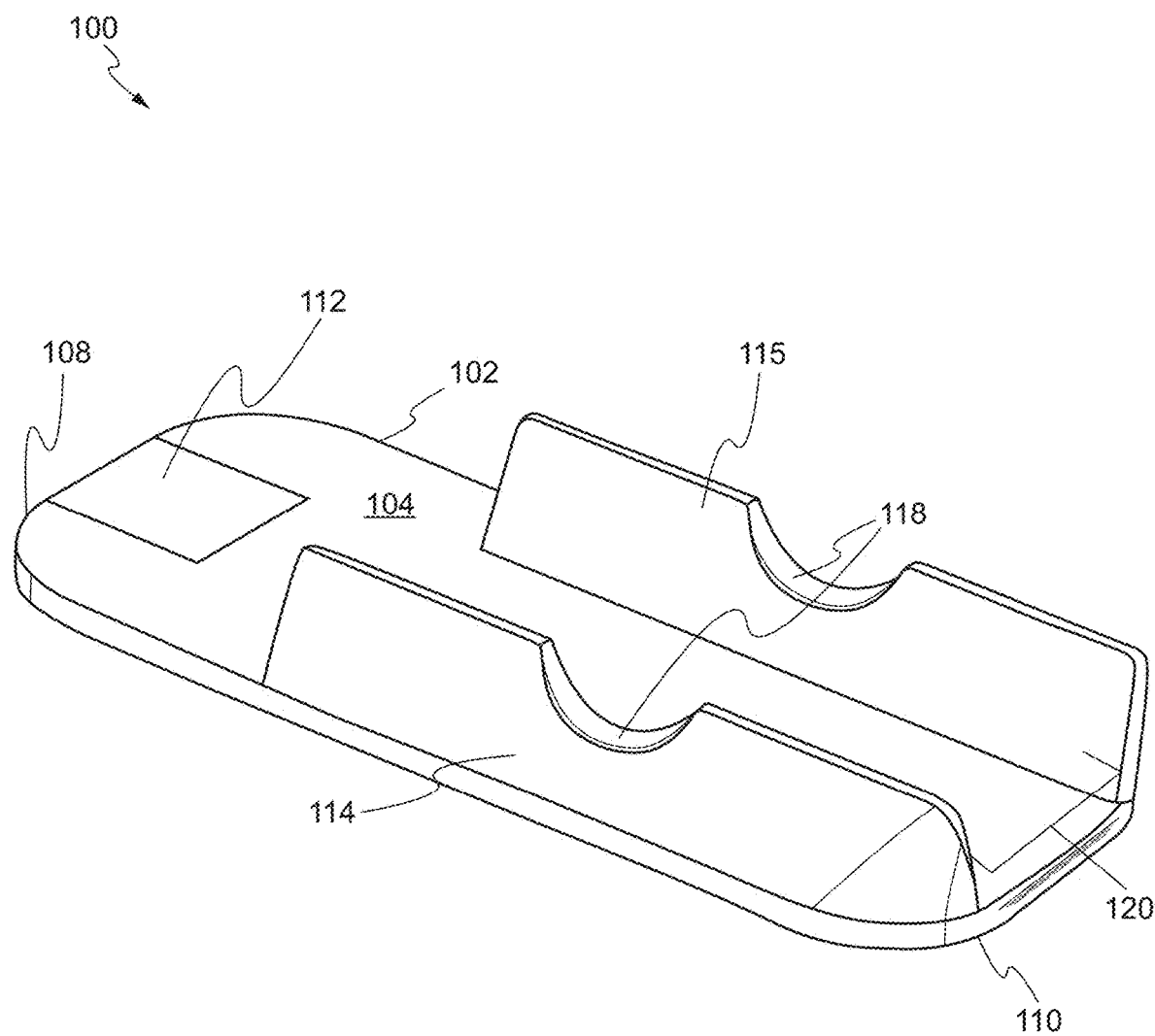
FIG. 4 shows a perspective view of the device, in a second state, according one embodiment of the present invention.

FIG. 4 shows the device, in a second state, according to one embodiment. In the second state, the one or more balloons 114, 115 are inflated (described below). The distal end 110 of the main body 102 is configured to deform to be substantially planar when each of the one or more balloons 114, 115 is inflated. As the one or more balloons 114, 115 are inflated, the increased pressure from the one or more balloons 114, 115 applies a force sufficient to flatten the distal end 110 of the main body 102. For example, the one or more balloons are inflated to a pressure that flattens the distal end 110 to a substantially planar, flat position that is flush with the proximal end 108. In another embodiment, the distal end 110 of the main body 102 is deformed, but may still have some curvature.

In some embodiments, the device 100 includes one or more channels that attach each of the one or more balloons 114, 115 to an inflation control configured to inflate the one or more balloons. For example, the channel can be a thin catheter tube that can supply a fluid to the one or more balloons 114, 115 via a pump or syringe. In some embodiments, a bifurcated catheter tube ("Y-tube") can be attached to each of the one or more balloons with a lower fitting. The distal end of the catheter tube can be attached to the one or more balloons 114, 115 and the proximal end of the catheter tube can be attached to a pump or fluid filled syringe. The pump or syringe can inflate the one or more balloons 114, 115 by filling it with fluid to a desired degree of expansion or pressure and then deflate the balloon by withdrawing the fluid.

In some embodiments, the one or more balloons 114, 115 are angioplasty balloons made of relatively strong but generally elastic material that can be folded into a compact, small diameter cross section. Due to the need for strength and stiffness, the one or more balloons 114, 115 may be rated to high pressures, depending on the diameter. In other embodiments, the one or more balloons 114, 115 comprise soft, very elastic material (e.g., natural rubber latex) as the balloon. Latex and other highly elastic materials generally will expand continuously upon increased internal pressure until the material bursts. As a result, these balloons are generally rated by volume in order to properly distend to a desired size. Although relatively weak, these balloons do have the advantage that they tend to readily return to their initial size and dimensions following inflation and subsequent deflation. It is also contemplated that the balloons can also be made of any medical grade balloon materials, for example, polyurethane or polyethylene terephthalate. In some embodiments, the one or more balloons 114, 115 are relatively small, e.g., a diameter in a range from 1 mm to 5 mm and a length in a range from 5 mm to 30 mm.

In some embodiments, each of the one or more balloons 114, 115 is provided in an elastic cover. When each of the one or more balloons 114, 115 is inflated in the second state, the elastic cover expands to the size of the balloon. During inflation, the one or more balloons 114, 115 exert a force to deform the distal end of the main body 102. In some embodiments, inflating the one or more balloons 114, 115 deform the distal end 110 of the main body 102 from an arcuate configuration to a substantially flat, planar configuration.

Figure 5:
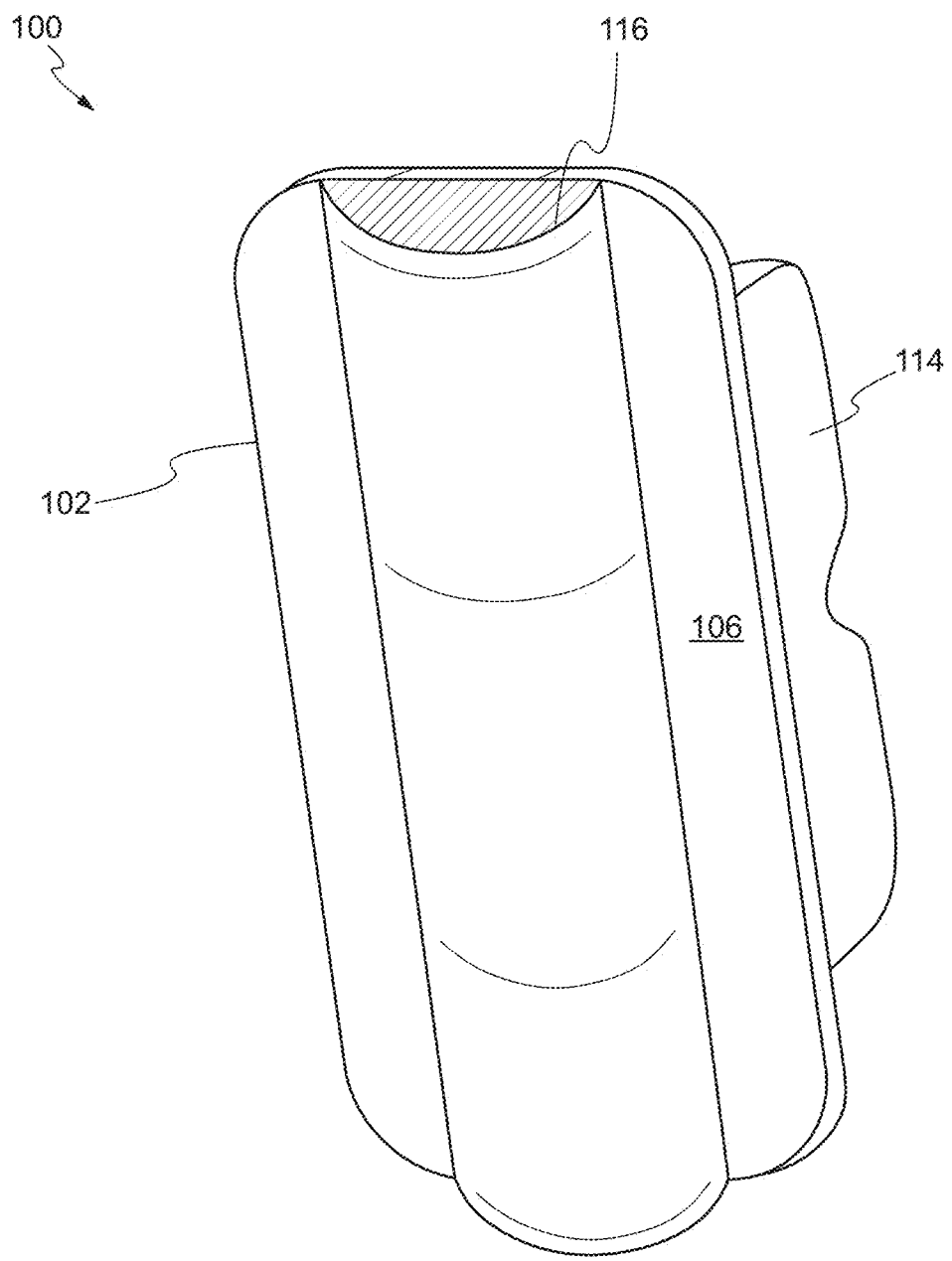
FIG. 5 shows a rear perspective view of the device, in a second state, according another embodiment of the present invention.

FIG. 5 shows a rear perspective view of the device, in a second state, according to one embodiment. In some embodiments, the rear face 106 of the main body 102 includes an additional balloon 116. The additional balloon 116 may be a hemostatic balloon. In some embodiments, the additional balloon 116 is deflated in the first state and is inflated in the second state. During surgery, if any bleeding occurs, the additional balloon 116 can apply a pressure to staunch any bleeding. In this respect, the additional balloon 116 can be selectively inflated and deflated during laparoscopic procedures. After bleeding has stopped, the additional balloon 116 can be deflated. The additional balloon 116 can also include a channel that attaches to an inflation control as described above. In some embodiments, the channel for the additional balloon 115 is separate from the channel of the one or more balloons 114, 115. The additional balloon 116 can be independently inflated via the inflation control.

Figure 6:
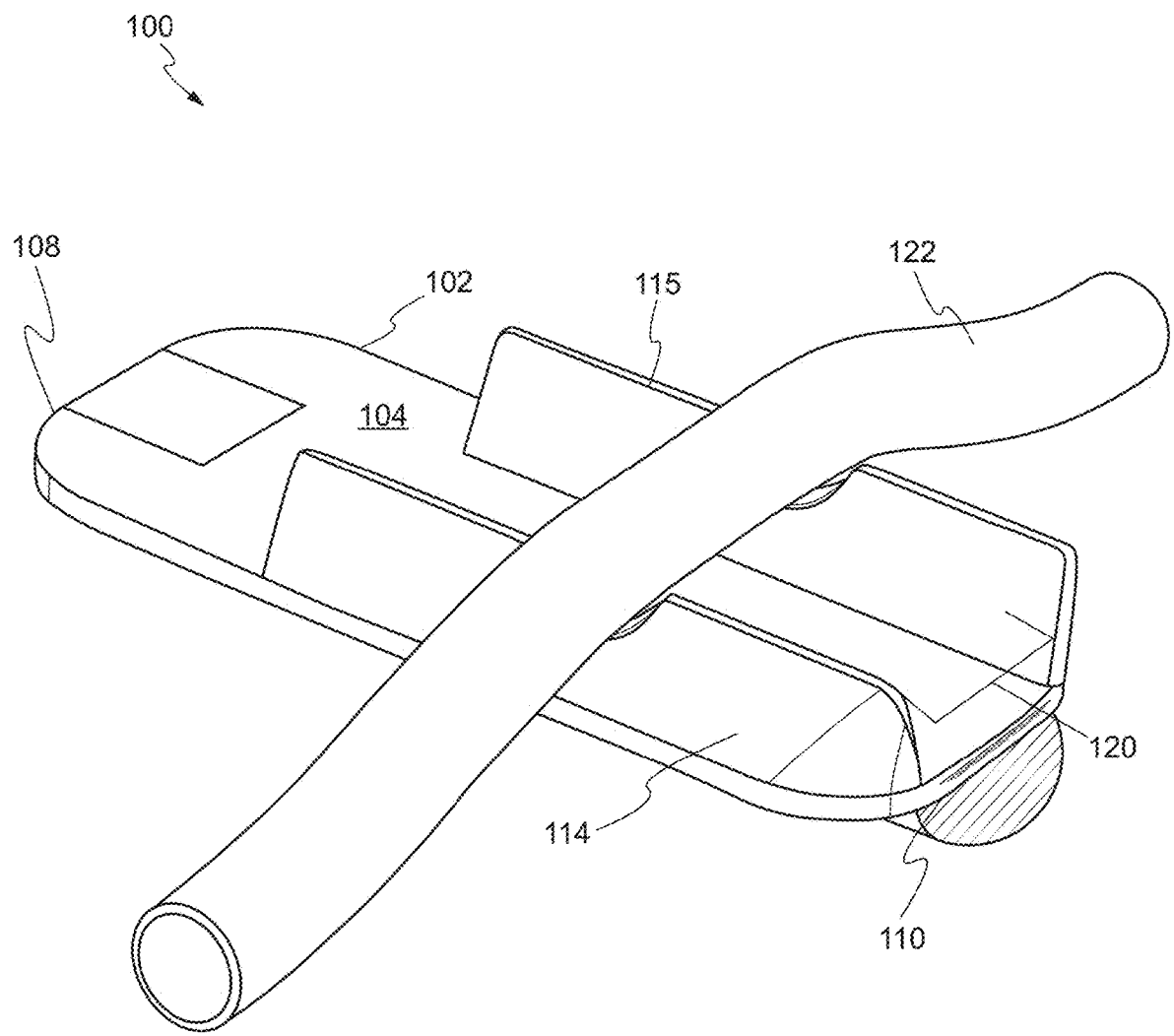
FIG. 6 shows the device supporting a target biological structure according one embodiment of the present invention.

FIG. 6 shows a target biological structure supported on the device according to one embodiment. In one embodiment, the one or more balloons 114, 115 comprise a first balloon 114 on a first side of the main body 102 and a second balloon 115 on a second side of the main body 102. The first side and the second side are edges between the proximal end 108 and the distal end 110 of the main body 102. In the second state, a channel 120 exists between the first balloon 114 and the second balloon 115. In the second state, the first balloon 114 and the second balloon 115 support a target biological structure 122 above the front face 104 of the main body 102. The channel 120 is located below the target biological structure 122 to allow a tool to access the target biological structure from multiple directions.

In Use

In one embodiment, a method for partly isolating a target biological structure is provided. The method may include making an incision in a patient. In some embodiments, the incision is a laparoscopic incision in the abdominal area of a patient. In use, the device may be introduced into the abdominal cavity of a patient through an incision or, alternatively, through a trocar or cannula device which is inserted into the incision for keeping the incision open.

After an incision is made, a device, in the first state, is inserted through the incision to access the target biological structure. For example, the device can be inserted through the incision by threading the device over a guidewire to the target biological structure. In some embodiments, the device may be a device having one or more of the characteristics described above. For example, the device may include a main body and one or more balloons disposed on a distal end of the main body. The main body may include a front face and a rear face having proximal and distal ends. The distal end of the device may have a first state and a second where the distal end is arcuate in a first state and is substantially planar in a second state. In a first state, each of the one or more balloons may be deflated. In a second state, each of the one or more balloons may be inflated. The distal end of the main body is configured to deform to be substantially planar when each of the one or more balloons on the front face are inflated in the second state.

After the device is inserted through the incision, the device is at least partially positioned beneath a target biological structure in the patient. For example, the distal end is positioned beneath the target biological structure. The device is then transitioned from the first state to the second state by at least partly inflating each of the one or more balloons. The inflation of the one or more balloons applies a pressure to the distal end which flattens the distal end to substantially planar configuration that may be flush with a planar proximal end. After inflation, the target biological structure is at least partly supported by each of the one or more balloons. In some embodiments, the transition from the first state to the second state is further caused by inflating an additional balloon disposed on a rear face of the main body, wherein the additional balloon is a hemostatic balloon. In some embodiments, the hemostatic balloon is inflated before each of the one or more balloons.

In some embodiments, the one or more balloons comprises a first balloon on a first side of the main body and a second balloon on a second side of the main body. The first side and the second side are between the proximal end and the distal end of the main body. In the second state, a channel exists between the first balloon and the second balloon. The target biological structure may be supported on the first balloon and the second balloon above the channel. In some embodiments, the method may further include inserting a tool in the channel for accessing the target biological structure.

In some embodiments, the device can remain substantially firm at room temperature, and its insertion through the incision or the trocar is smooth and unobstructed. However, once the device is inserted into the abdomen, the flexible thermoplastic material of the device may become more susceptible to deforming. The change in rigidity of the device may be due to the relationship between properties of the material comprising the device, e.g., glass transition temperature, and the body temperature of the patient. In this regard, if the device is formed of PEEK plastic which has a relatively high glass transition temperature, this can be avoided.

According to this embodiment, the device, in a first state, may be inserted into a patient's abdomen through a small incision. Then, when the device is positioned near the target biological structure, the balloons of the device can be in inflated in the second state. In the second state, the balloons on the main body are inflated and functions to both isolate and support the target biological structure thereon. Finally, the balloons can be deflated back to the first state and removed via the incision.

In use, the device isolates and positions a target biological structure. In the second state, the one or more balloons function to flatten the distal end of the device. The one or more balloons elevate the target biological structure above the front face of the main body and provides a channel below the target biological structure. The rear face includes a hemostatic balloon to provide pressure around the retractor body to stanch bleeding from surrounding structures.

It is recognized that the devices may be constructed in a number of configurations, which satisfy the primary objective of providing an inflatable, atraumatic laparoscopic device. The devices described above may be used in a wide variety of applications using traditional trocar and cannula designs which range from about 5-12 mm. Of course, the dimensions of the device and the specific shape of the devices, including the balloons, may be specially adapted to address particular circumstances.

Rigid Device

Figure 7:
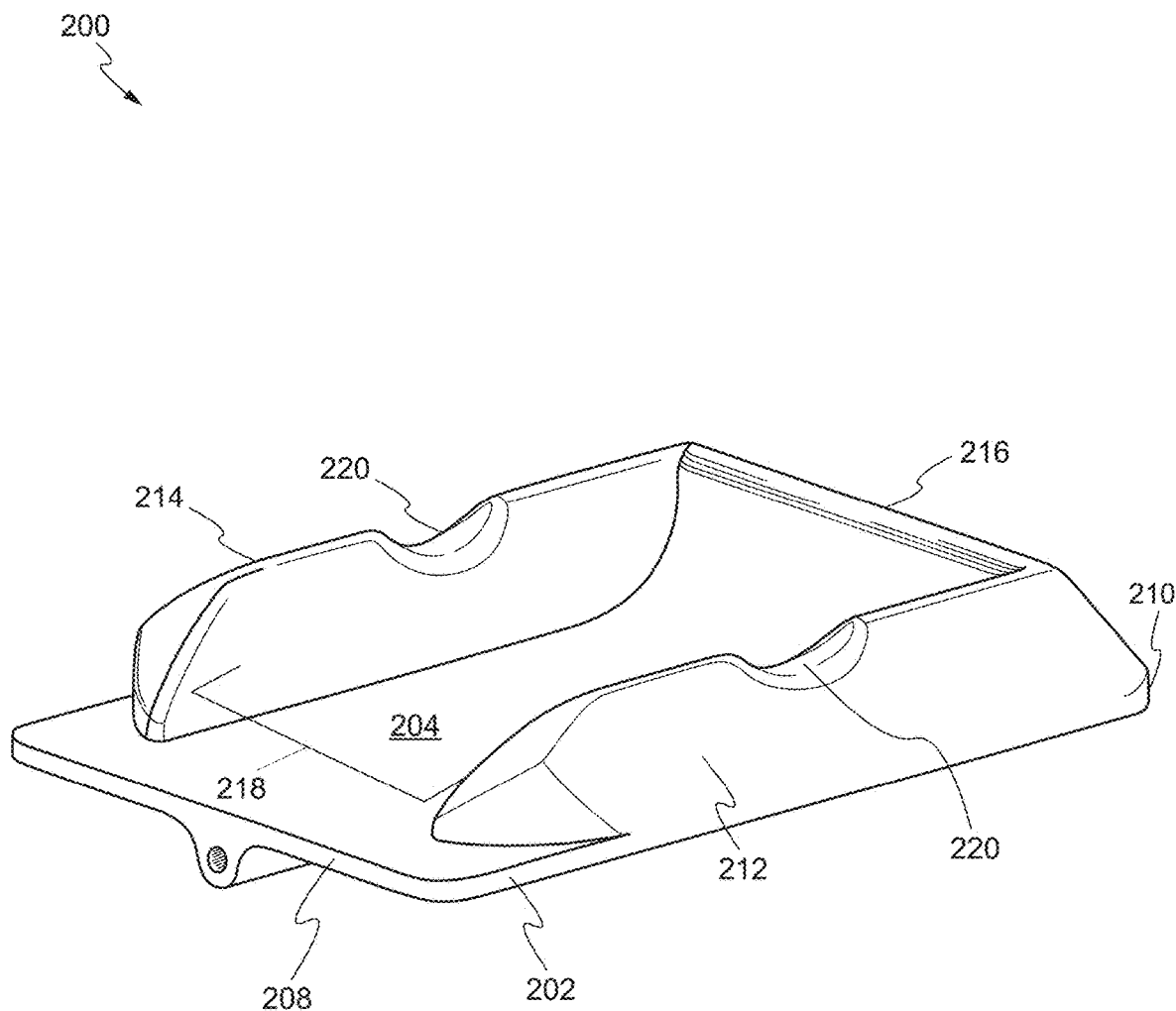
FIG. 7 shows a front perspective view of a device according to another embodiment of the present invention.
Figure 8:
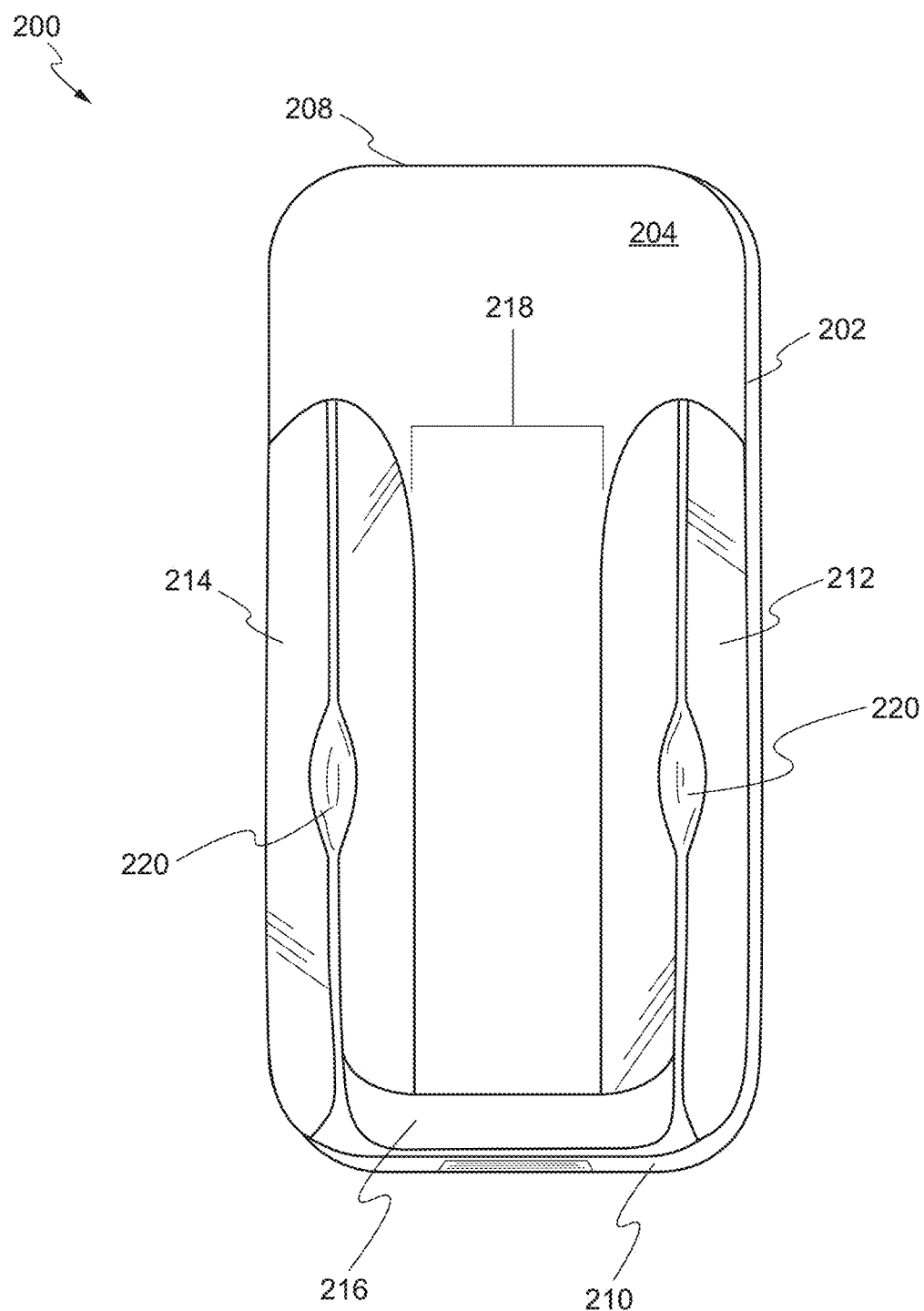
FIG. 8 shows an overhead view of the device according to one embodiment of the present invention.

FIGS. 7 and 8 show front and overhead views of a device, respectively, according to another embodiment. The device 200 comprises a base plate 202 including a front face 204, a rear face 206, a proximal end 208, and a distal end 210. On the front face 204 of the base plate 202, a first sidewall 212 is disposed on a first end and a second sidewall 214 is disposed on an opposing second end. In some embodiments, the device 200 comprises a single, unitary structure formed of a thermoplastic material (as described above). In other embodiments, the device 200 is formed of a rigid material that does not deform.

The device 200 further includes an end wall 216 on the distal end 210 of the base plate 202. In some embodiments, the end wall 216 is on the distal end 210 of the base plate 202 between the first sidewall 212 and the second sidewall 214. The end wall 216 is inclined relative to the proximal end 208 of the base plate 202. The proximal end 208 of the base plate 202 is substantially planar. In some embodiments, the end wall 216 has an incline of at least 30 degrees or more relative to the proximal end 208, e.g., 40 degrees or more, 50 degrees or more, 60 degrees or more, 70 degrees or more, 80 degrees or more, or 90 degrees or more. In some embodiments, the end wall 216 may have an arcuate curvature. The end wall 216 spans the width of the base plate 202 and bridges the first sidewall 212 and the second sidewall 214 at the distal end 210 of the base plate 202.

The first sidewall 212 and the second sidewall 214 form a channel 218 therebetween. The channel 218 is a region between the sidewalls that provides access to the target biological structure. In some embodiments, the first sidewall 212 and the second sidewall 214 each include a recess 220 on a portion of a surface of each of the first sidewall 212 and the second sidewall 214 that is opposing the front face 204 of the base plate 202. The recess 220 is configured to isolate and support the target biological structure above the channel 218. The target biological structure can be a vessel, artery, nerve, tissue or organ of the patient.

In some embodiments, a proximal end of the first sidewall 212 and the second sidewall 214 is approximately normal to the proximal end 208 of the base plate 202. The proximal end of the first sidewall 212 and the second sidewall 214 may each comprise a nose-like structure, e.g., a rounded projection, to separate tissues and other vasculature from the target biological structure. The proximal end 208 of the base plate 202 is substantially planar. In some embodiments, the device 200 may include a handle on the proximal end 208 of the base plate 202. For example, the handle may be a grasper configured to be grasped by Maryland forceps.

Figure 9:
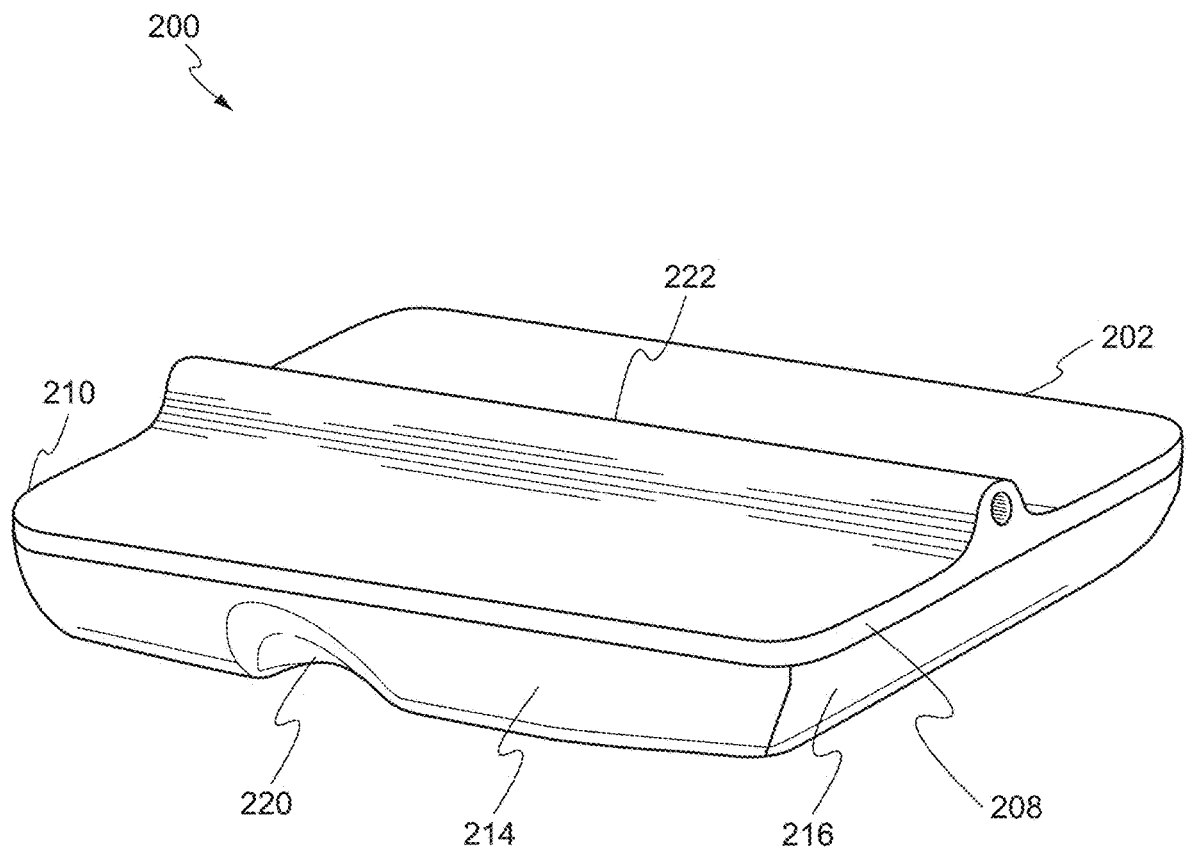
FIG. 9 shows a rear perspective view of the device according to one embodiment of the present invention.

FIG. 9 shows a rear perspective view of the device according to another embodiment. As shown in FIG. 9, the device 200 may further comprise a conduit 222 on the rear face 206 of the base plate 202. The conduit 222 may extend the entire length of the base plate 202. The conduit 222 is configured to receive a guidewire therethrough. As such, the device 200 can be threaded over the guidewire to a target biological structure.

In one embodiment, a method for partly isolating a target biological structure is provided. The method may include making an incision in a patient. In use, the device may be introduced into the abdominal cavity of a patient through a laparoscopic incision or, alternatively, through a trocar or cannula device which is inserted into the incision in the patient's body.

After an incision is made, a device is inserted through the incision to access the target biological structure. In some embodiments, the rear face of the base plate comprises a conduit configured to receive the guidewire. In this way, the device can be inserted through the incision by threading the device over a guidewire to the target biological structure. In some embodiments, the device includes: a base plate comprising a front face and a rear face, the base plate having proximal and distal ends; a first sidewall positioned on a first end of the front face and a second sidewall disposed on an opposing second end of the front face, wherein a channel exists between the first sidewall and the second sidewall; and an end wall positioned on the distal end of the main body between the first sidewall and the second sidewall. The end wall is inclined relative to the proximal end of the base plate.

After the device is inserted through the incision, the device is positioned at least partially beneath a target biological structure in the patient. The target biological structure is supported on the first sidewall and second sidewall above the base plate. In some embodiments, the first sidewall and the second sidewall include a recess for isolating the target biological structure above a channel formed between the sidewalls. A user can insert a tool in the channel to access the target biological structure. In some embodiments, the angle of the tool can be adjusted by contacting the tool with the end wall.

The design of each of the devices advantageously allows a user to partly isolate a target biological structure and more easily access all areas of the target biological structure from multiple directions. In this way, during laparoscopic procedures, a user can modify, e.g., ligate, incise, or attach tools, to target biological structures. The device advantageously allows a user to separate tissue and surrounding structures from the target biological structure, position and retain a target biological structure, create a working space underneath and around the target biological structure, and an end wall for turnaround of surgical tools.

Method of Placing a Cuff on a Target Biological Structure

The present disclosure further relates to a method for placing a cuff on a target biological structure in a patient. In some embodiments, the method provides access to the target biological structure, e.g., the splenic artery, using laparoscopic devices that are guided over a guidewire. The method provides an atraumatic technique to support and partly isolate the target biological structure away from surrounding biological structures, e.g., the pancreas, to place a cuff around the target biological structure. For example, the method may temporarily elevate the target biological structure away from surrounding biological structures to place one or more cuffs on the target biological structure with minimal damage to the surrounding biological structures.

In the illustrative embodiments discussed below, the method may be discussed in the context of positioning an artery, e.g., the splenic artery, from a neurovascular bundle near the pancreas. However, the methods disclosed herein can be used in any laparoscopic procedure. The method enables a user to partly isolate, i.e., pull away or separate, a target biological structure from surrounding structures, without causing trauma to the surrounding structures or the target biological structure to place a cuff thereon.

FIGS. 10-13 show exemplary embodiments of preparing a surgical site (e.g., the splenic artery) for a surgical procedure. More specifically, a ramp device and a cuff device are used to isolate the target biological structure to enable surgical access to at least part of the target biological structure from its biological surroundings. FIGS. 10-29 and 31-35 illustrate steps for performing this isolation.

Figure 10:
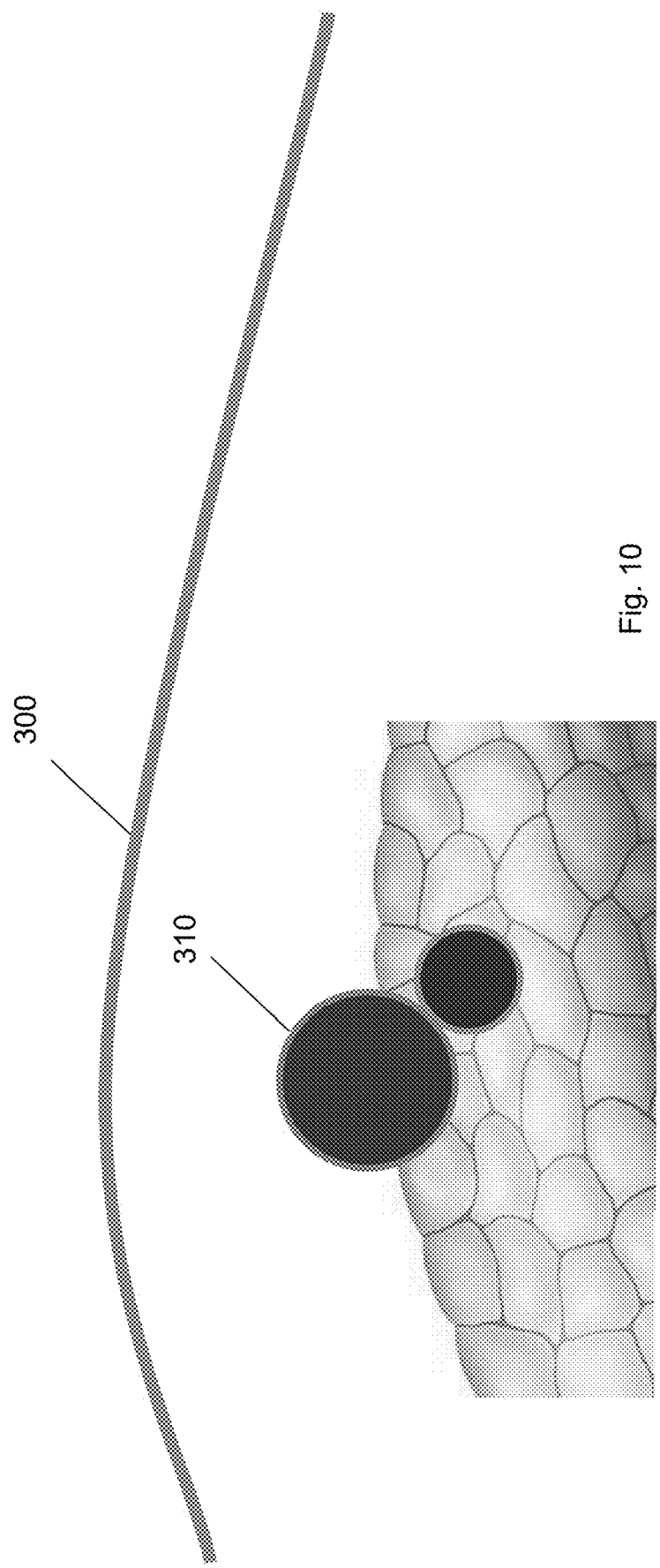
FIG. 10 shows the skin of a patient and a target biological structure underneath the skin according to one embodiment of the present invention.

FIG. 10 shows the skin 300 of the patient and the target biological structure 310 underneath the skin. The method may begin by making one or more incisions in the skin 300 of a patient to access the target biological structure 310 underneath the skin 300. In one instance, the one or more incisions may be near the abdominal region of a patient. In some embodiments, the one or more incisions may have a diameter in the range from 1 mm to 10 mm, e.g., from 2 mm to 8 mm or from 4 mm to 6 mm.

Figure 11:
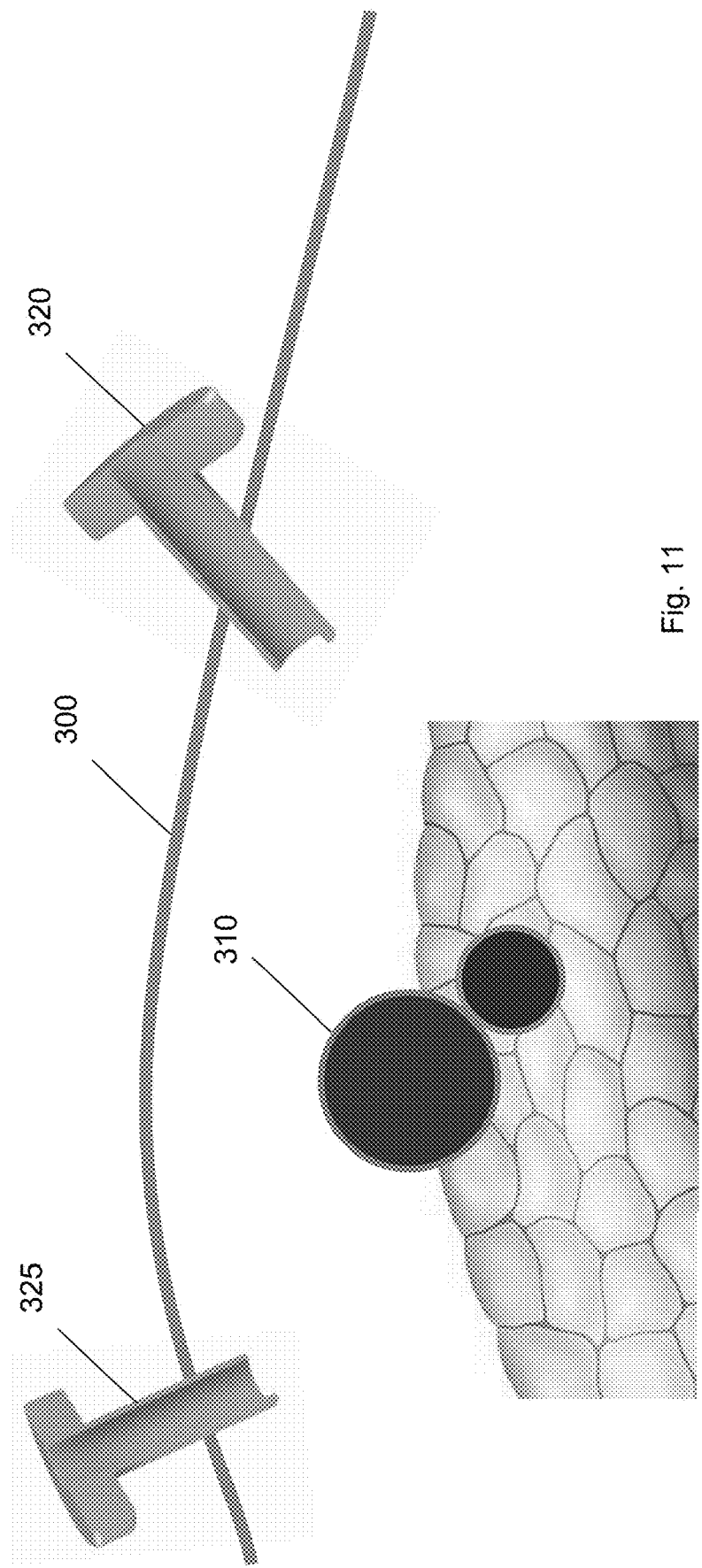
FIG. 11 shows trocars inserted into incisions in the skin according to one embodiment of the present invention.

FIG. 11 shows trocars inserted into two incisions in the skin 300 of the patient. After making incisions through the skin 300, the incisions may be enlarged with a medical tool, e.g., a scalpel, to accommodate trocars 320, 325 in each of the incisions. Trocars, e.g., a first trocar 320 and a second trocar 325, used in this method typically comprise a hollow-bore cannula. The ends of trocars 320, 325 may be either a multi-faceted bevel or conical shape. The ends of the trocars 320, 325 are inserted into the incisions, and may be forced through the underlying fascial layer, e.g., in the abdomen, using a downward pressure and drilling motion. For example, the abdominal wall may be pierced to form an incision and a tubular trocar may be then inserted into the abdominal cavity.

Figure 12:
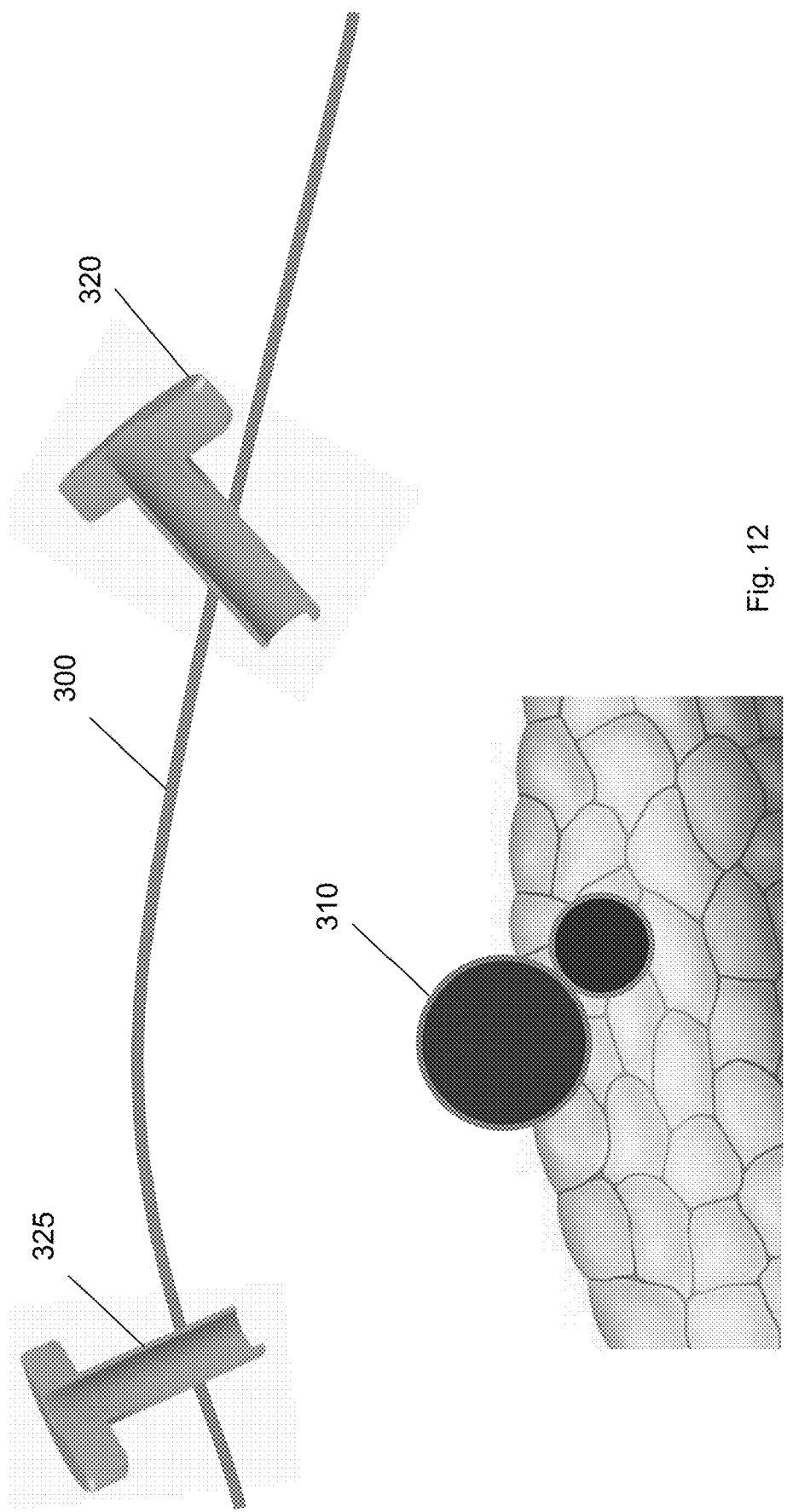
FIG. 12 shows an insufflated area beneath the skin according to one embodiment of the present invention.

FIG. 12 shows an insufflated area beneath the skin 300 according to one embodiment of the present invention. After the trocars 320, 325 are inserted into the incisions, a volume underneath the skin 300 is insufflated. The insufflation can include introducing a gas (e.g., $CO_2$ gas). In some embodiments, an insufflation device for delivering a gas is inserted into the trocars 320, 325 to enlarge the operative field to access the target biological structure 310. In some embodiments, when the incision is made in abdominal cavity of a patient, a needle is inserted through the one or more trocars. The needle may comprise a sharp needle having a lumen. By insufflating the area underneath the skin, it may retract the anterior abdominal wall exposing the operative field to the target biological structure.

Figure 13:
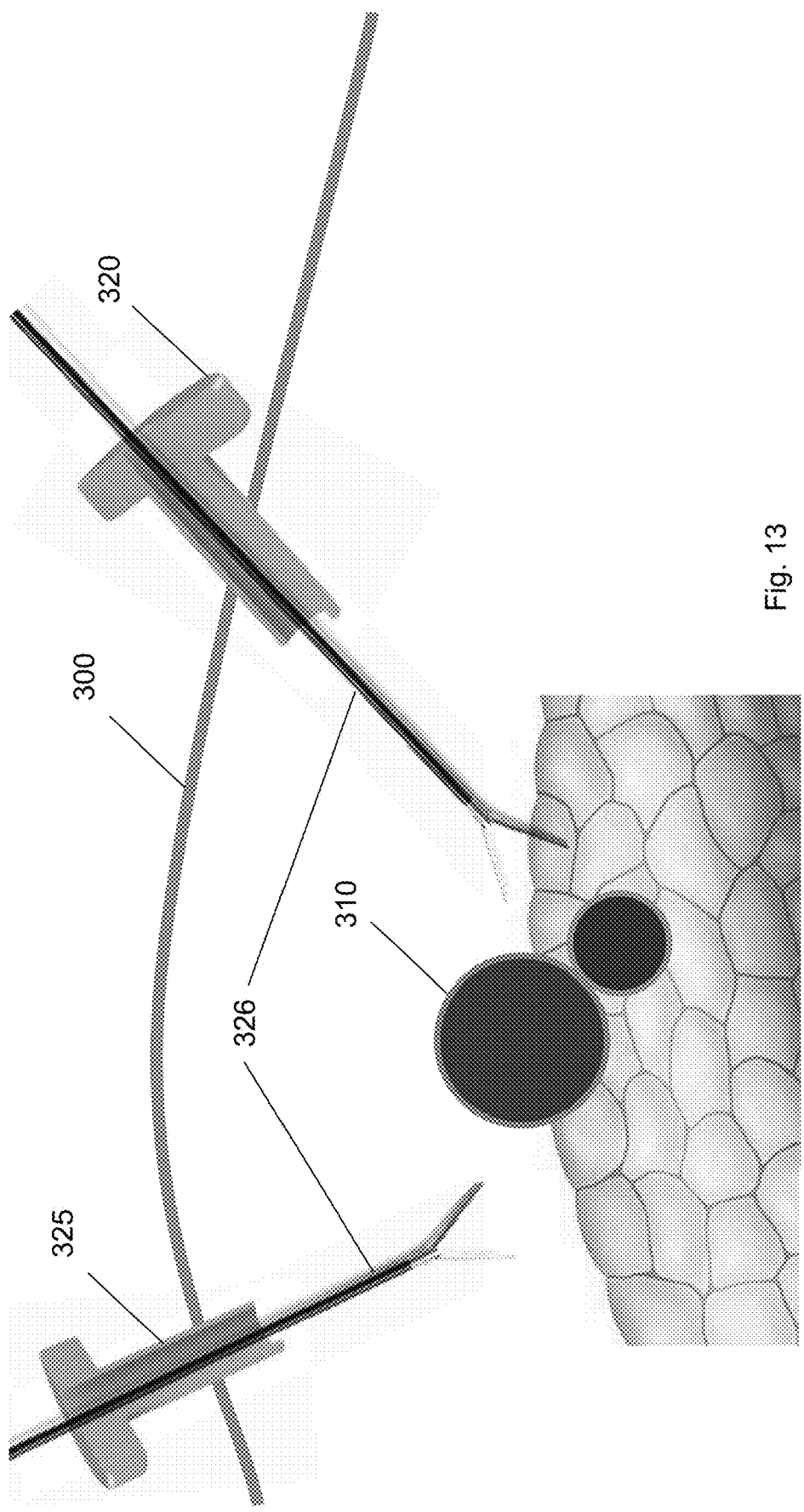
FIG. 13 shows laparoscopic tools inserted through the trocars for creating a path to the target biological structure according to one embodiment of the present invention.

FIG. 13 shows laparoscopic tools 326 placed through the trocars 320, 325 for creating a pathway to the target biological structure 310 according to one embodiment of the present invention. In some embodiments, after insufflation, the method may include using one or more laparoscopic tools 326 for manual dissection of biological structures to create a pathway to the target biological structure 310. The laparoscopic tools 326 may dissect the area underneath the skin 300 to provide a pathway to the target biological structure 310. For example, laparoscopic tools 326 such as graspers can be inserted through each of the trocars 320, 325 to move or dissect biological structures along natural tissue planes to provide a pathway to access the target biological structure 310. In other embodiments, laparoscopic tools, e.g., graspers, dissectors, scissors, retractors, etc., are placed through the trocars for manipulations of the operative field or target biological structure by the user, e.g., a surgeon.

Figure 14:
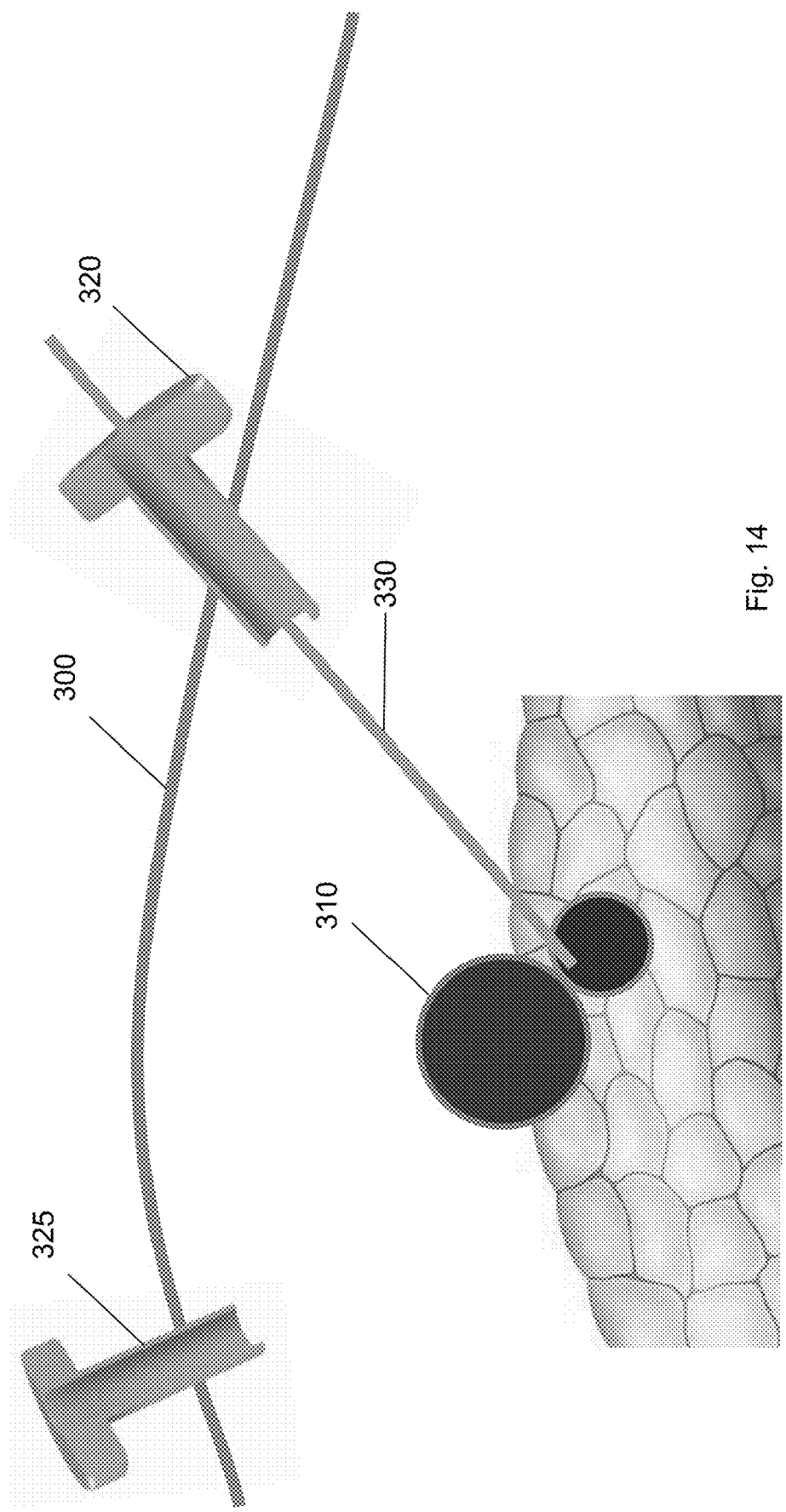
FIG. 14 shows a guidewire inserted through a first trocar to the target biological structure according to one embodiment of the present invention.
Figure 15:
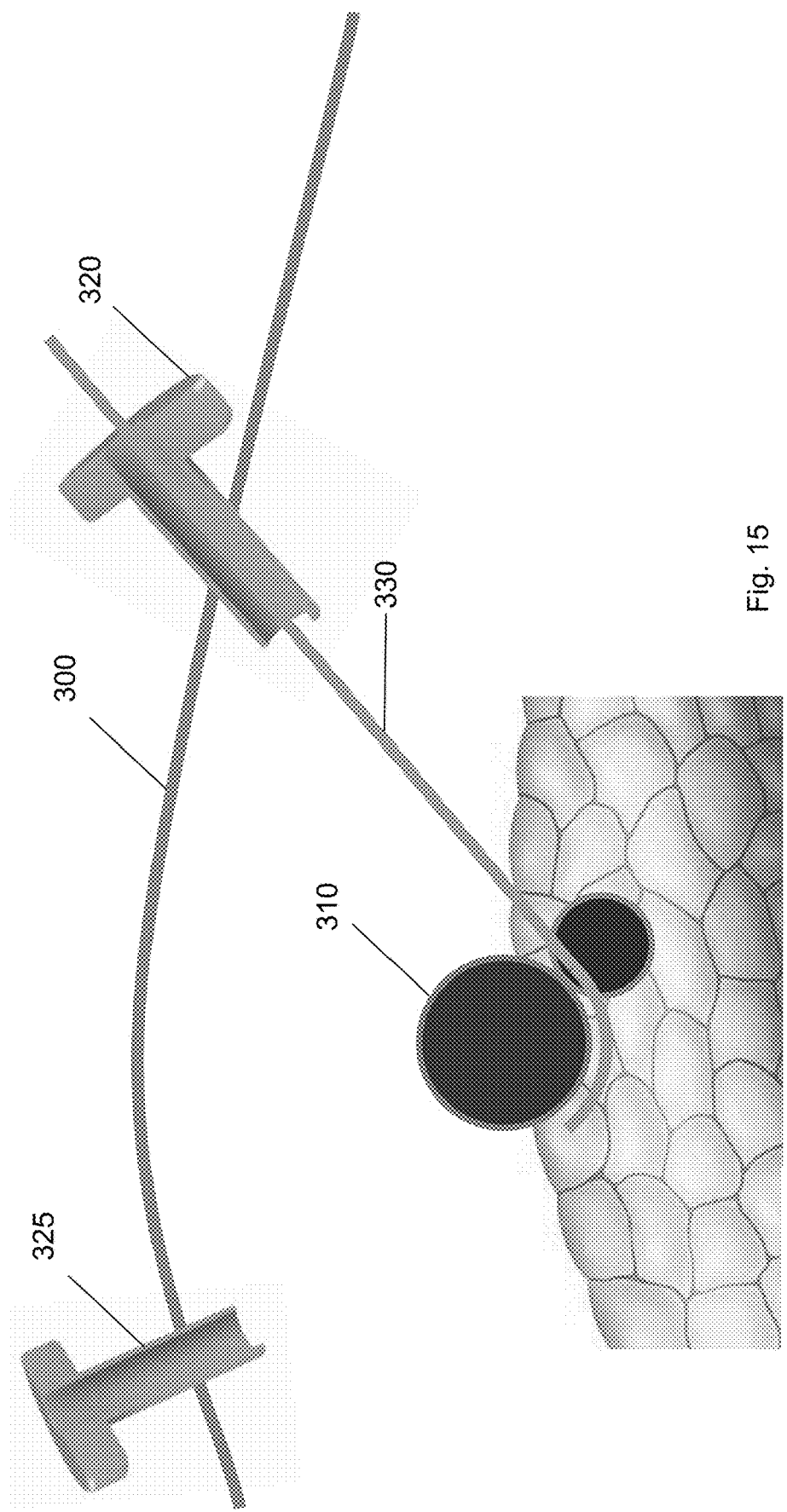
FIG. 15 shows the guidewire inserted from the first trocar to a position underneath the target biological structure according to one embodiment of the present invention.
Figure 16:
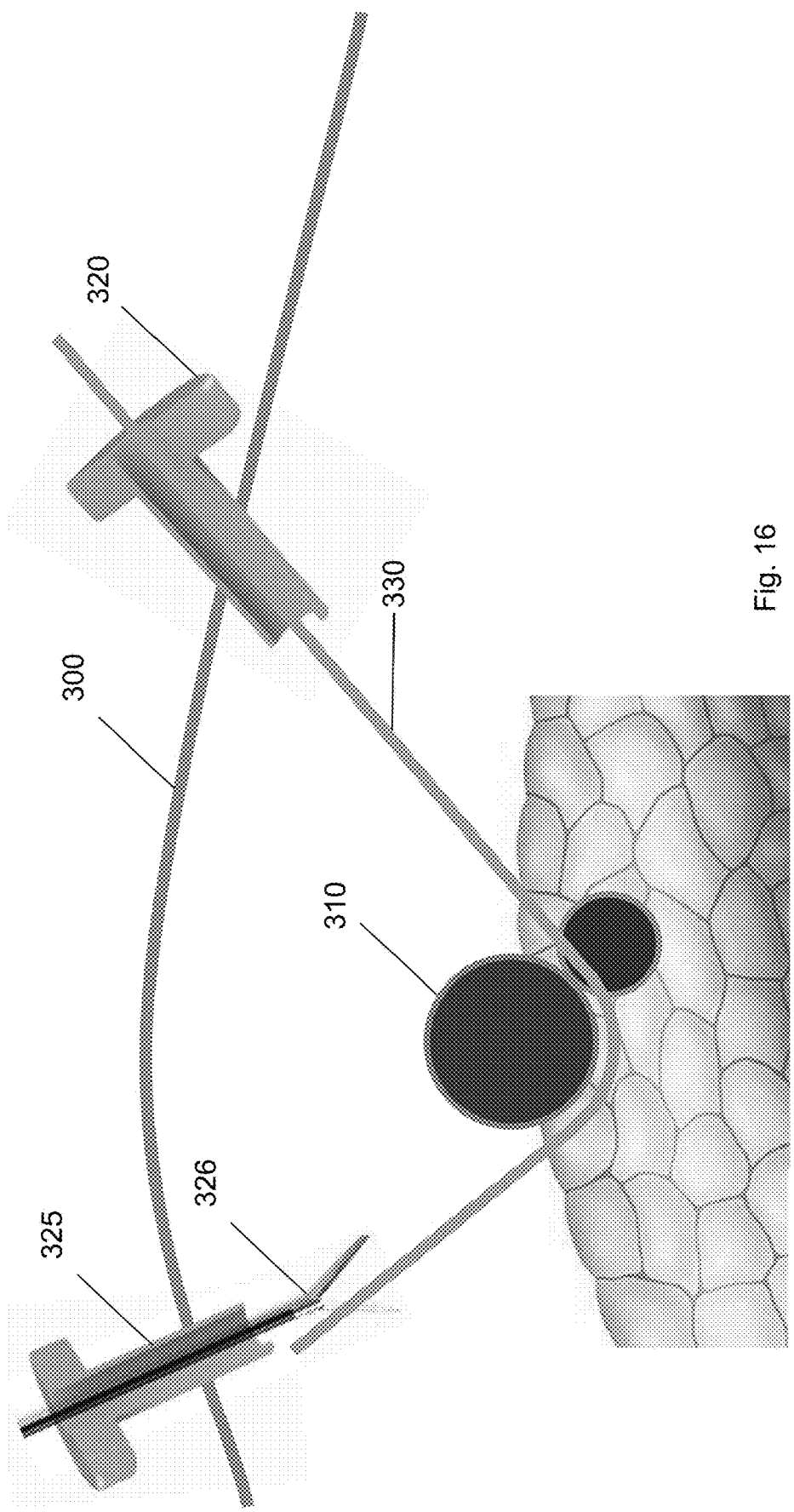
FIG. 16 shows the guidewire secured at the second trocar according to one embodiment of the present invention.

FIGS. 14-16 show the path of guidewire 330 inserted through a first trocar 320 to a position underneath the target biological structure 310 and then to the second trocar 325. A guidewire 330 may be inserted through the one or more trocars 320, 325 to provide a track for medical tools to access the target biological structure 310. For example, FIG. 14 shows the guidewire 330 inserted through the first trocar 320 towards the exterior surface of the target biological structure 310. In some embodiments, after manual dissection with the laparoscopic tools, the guidewire 330 is threaded through the pathway.

FIG. 15 shows the guidewire 330 passing underneath and around the target biological structure 310. The guidewire 330 includes a proximal end and a distal end. The proximal end may be an end of the guidewire 330 closest to the user and the distal end may be an end of the guidewire 330 which is furthest from the user. The distal end of the guidewire 330 may be inserted through the first trocar 320 to the target biological structure 310. In some embodiments, the distal end of the guidewire 330 includes an atraumatic tip 332. The atraumatic tip 332 of the distal end may have a curvature with respect to the long axis of the guidewire 330. For example, the tip of the distal end may be a floppy J-shaped tip. In some embodiments, the distal end of the guidewire 330 is configured to pass underneath and around the target biological structure 310.

From the position underneath the target biological structure 310, the guidewire 330 is then threaded to the second trocar 325. FIG. 16 shows the guidewire 330 threaded from the first trocar 320 to a position underneath the target biological structure 310 to the second trocar 325. The guidewire 330 may wrap around the target biological structure 310 structure to the second trocar 325. As shown in FIG. 16, a laparoscopic tool, e.g., a grasper, may be inserted through the second trocar 325 to secure the distal end of the guidewire 330. The grasping tool may guide the distal end of the guidewire 330 towards the second trocar 325. In some embodiments, tension may be applied to the guidewire 330 to move or position the target biological structure 310 away from surrounding biological structures.

Figure 17:
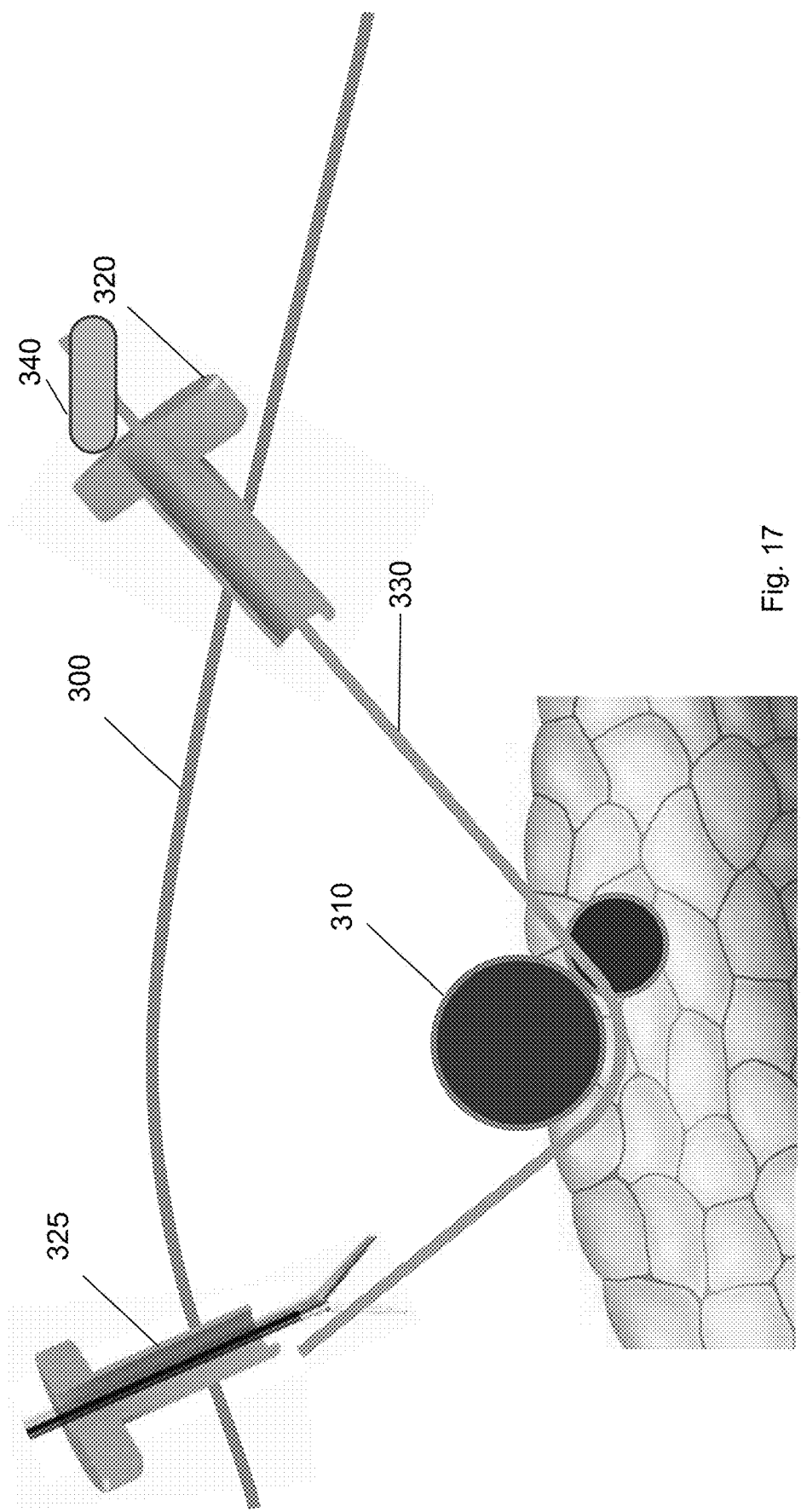
FIG. 17 shows a balloon tool inserted over the guidewire through the first trocar according to one embodiment of the present invention.
Figure 18:
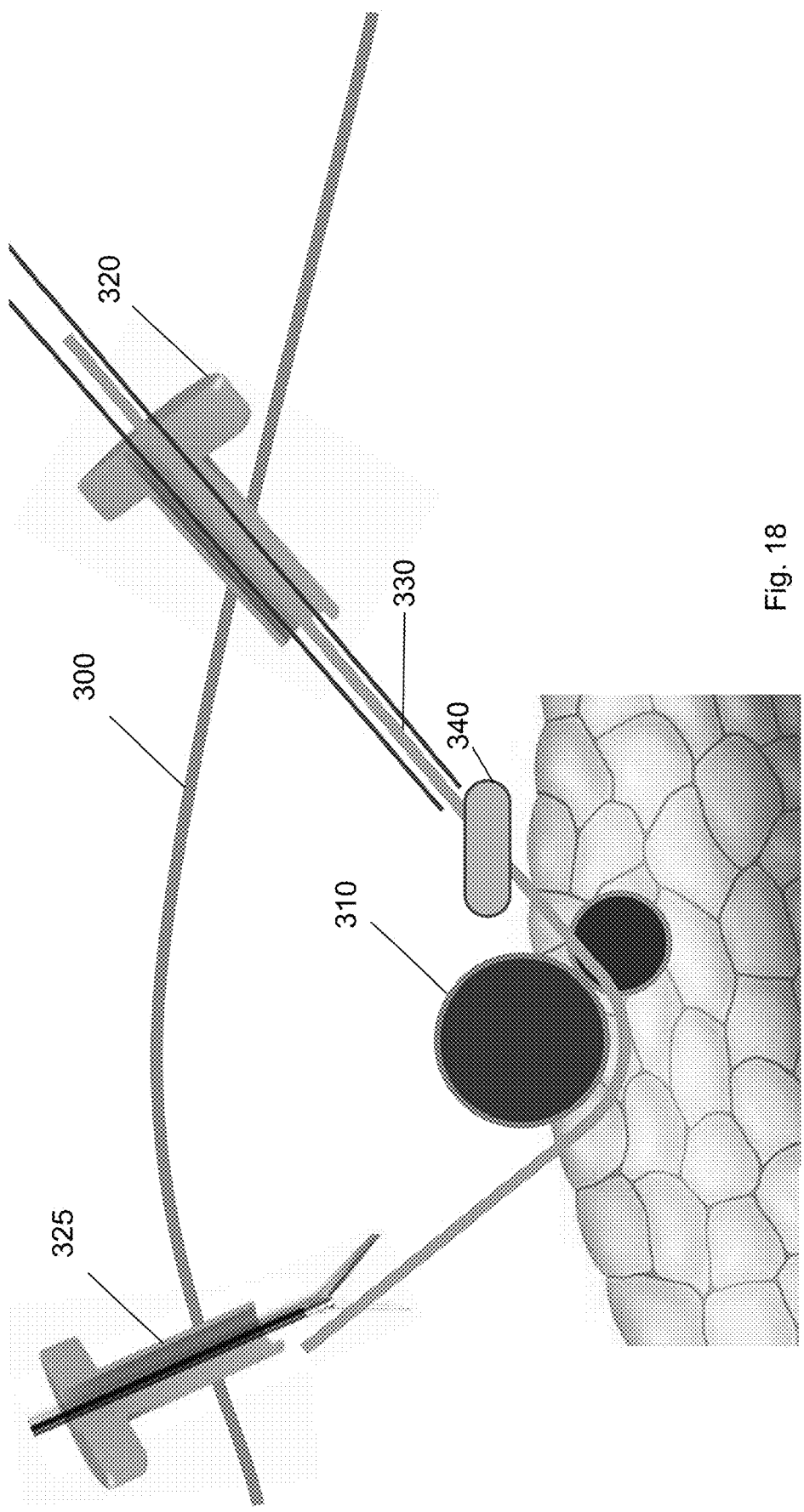
FIG. 18 shows the balloon tool at a position along the guidewire according to one embodiment of the present invention.
Figure 19:
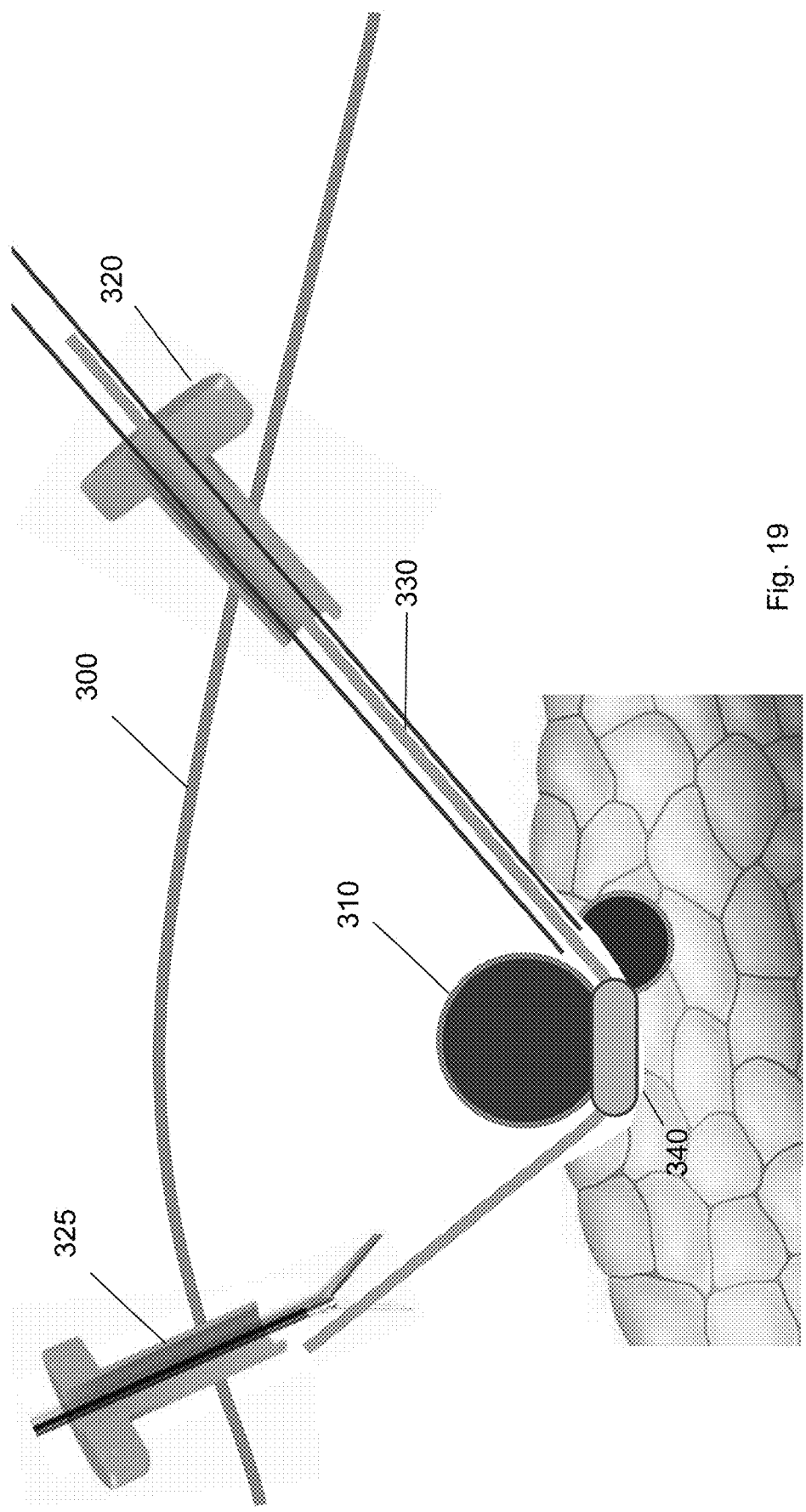
FIG. 19 shows the balloon tool guided to a position underneath the target biological structure according to one embodiment of the present invention.

FIGS. 17-20 show a balloon tool traversing over the guidewire 330 from the first trocar 320, to a position underneath the target biological structure 310, to the second trocar 325 according to embodiments of the present invention. Specifically, the balloon tool 340 may be inserted through the first trocar 320 over the guidewire 330. (FIG. 17.) The balloon tool 340 is guided over the guidewire 330 (FIG. 18) to a position underneath the target biological structure 310 (FIG. 19). The balloon tool 340 includes a balloon that may be inflated when the balloon tool 340 is at a position underneath the target biological structure 310 to provide pressure to the target biological structure 310. In this way, the target biological structure 310 may be separated from the surrounding biological structures, e.g., tissues, organs, or other vasculature, using the balloon tool 340. In particular, the balloon tool is capable of dissecting the blind area behind the target biological structure 310 without using conventional blunt dissection equipment.

Figure 20:
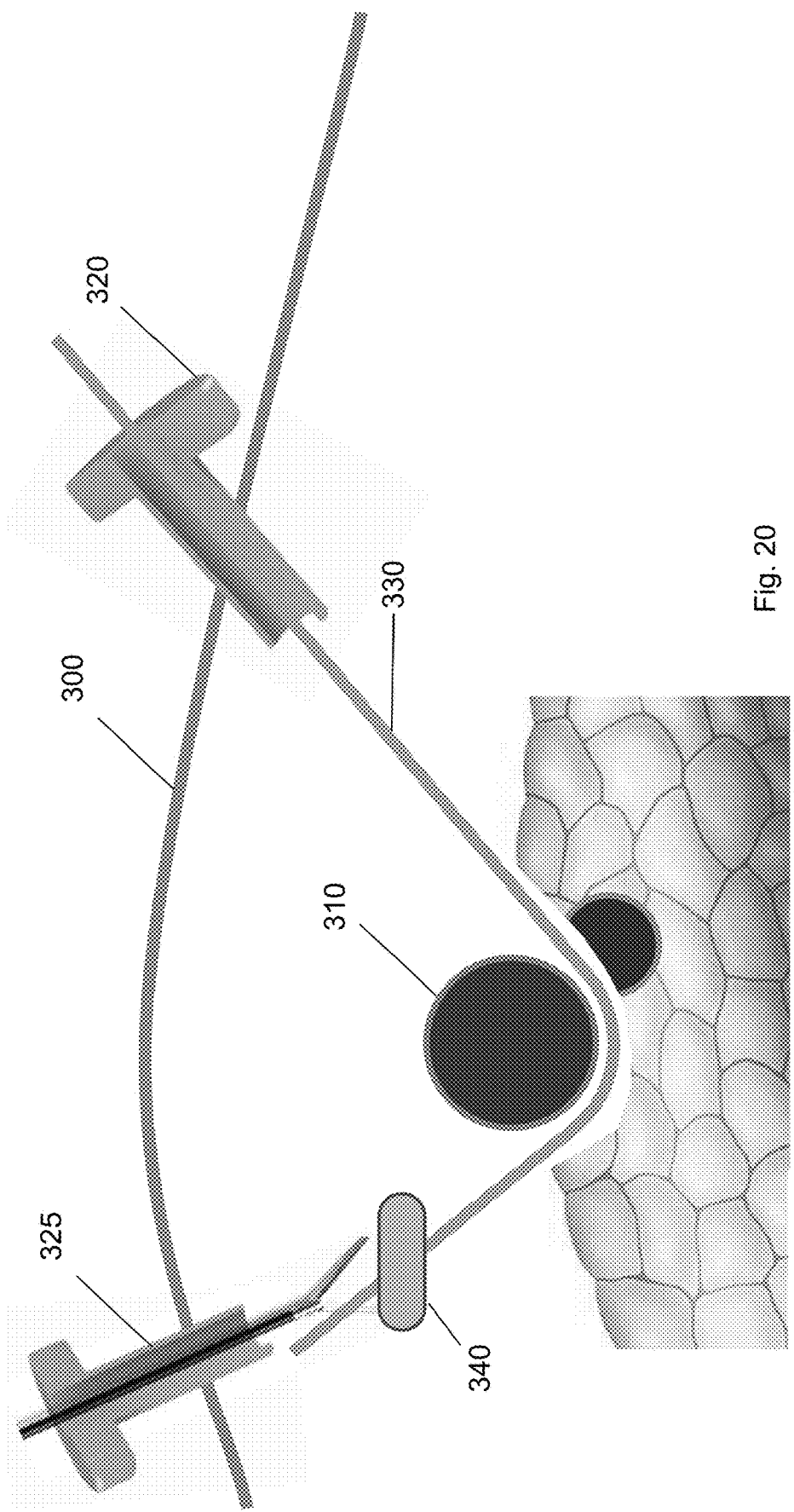
FIG. 20 shows the balloon tool guided to the second trocar according to one embodiment of the present invention.

In some embodiments, the balloon of the balloon tool 340 may be selectively inflated and deflated at a plurality of positions along the guidewire 330. For example, the balloon may be a hemostatic balloon that is inflated at a plurality of the positions along the guidewire 330. The balloon separates biological structures along natural tissue planes along the guidewire pathway to the target biological structure 310 and underneath the target biological structure 310. Finally, the balloon may be deflated and removed from the patient through the second trocar 325. (FIG. 20.)

Figure 21:
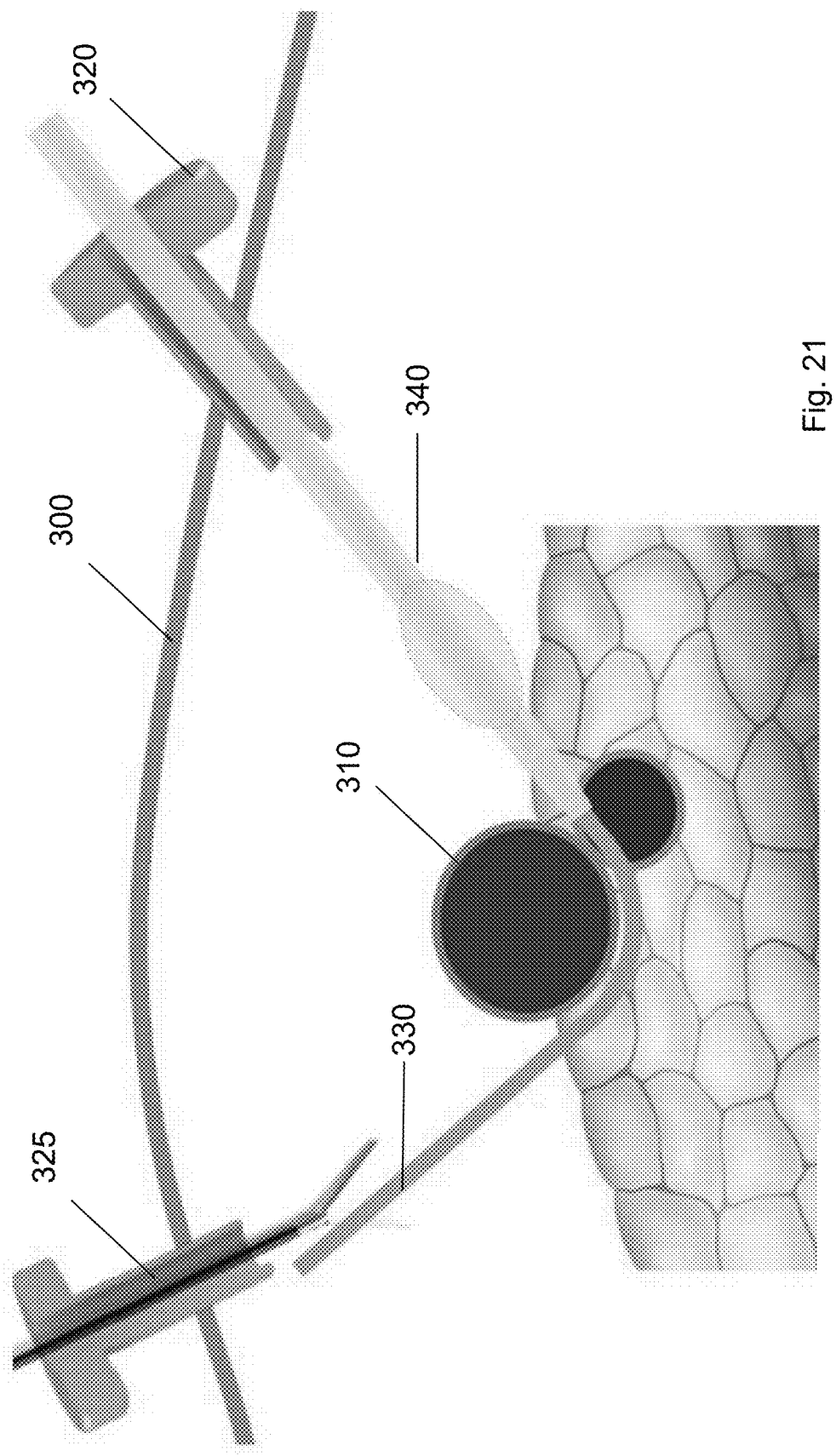
FIG. 21 shows the balloon tool according to one embodiment of the present invention.

FIG. 21 shows one embodiment of the balloon tool. In some embodiments, the balloon tool may be integrated with an over-the-wire dilatation catheter. The over-the-wire dilatation catheter tool can follow the guidewire down to the target biological structure and the balloon tool can be inflated and deflated at different positions along the guidewire. The dilatation catheter may include a tapered end to easily move along the guidewire without damaging surrounding biological structures. When dissection is completed, the deflated balloon can be withdrawn along with dilation catheter.

Figure 22:
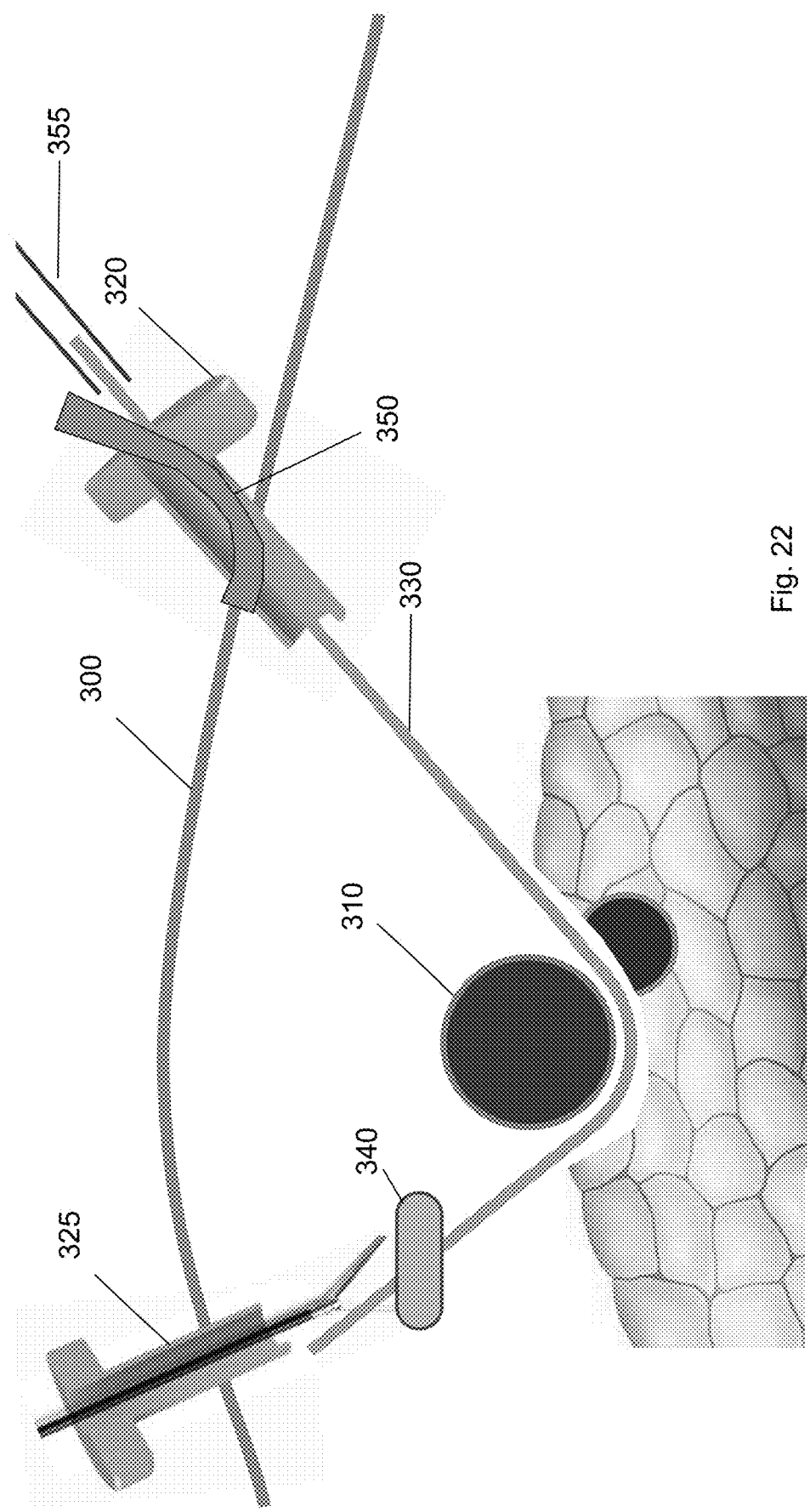
FIG. 22 shows a ramp device guided over the guidewire through the first trocar according to one embodiment of the present invention.
Figure 23:
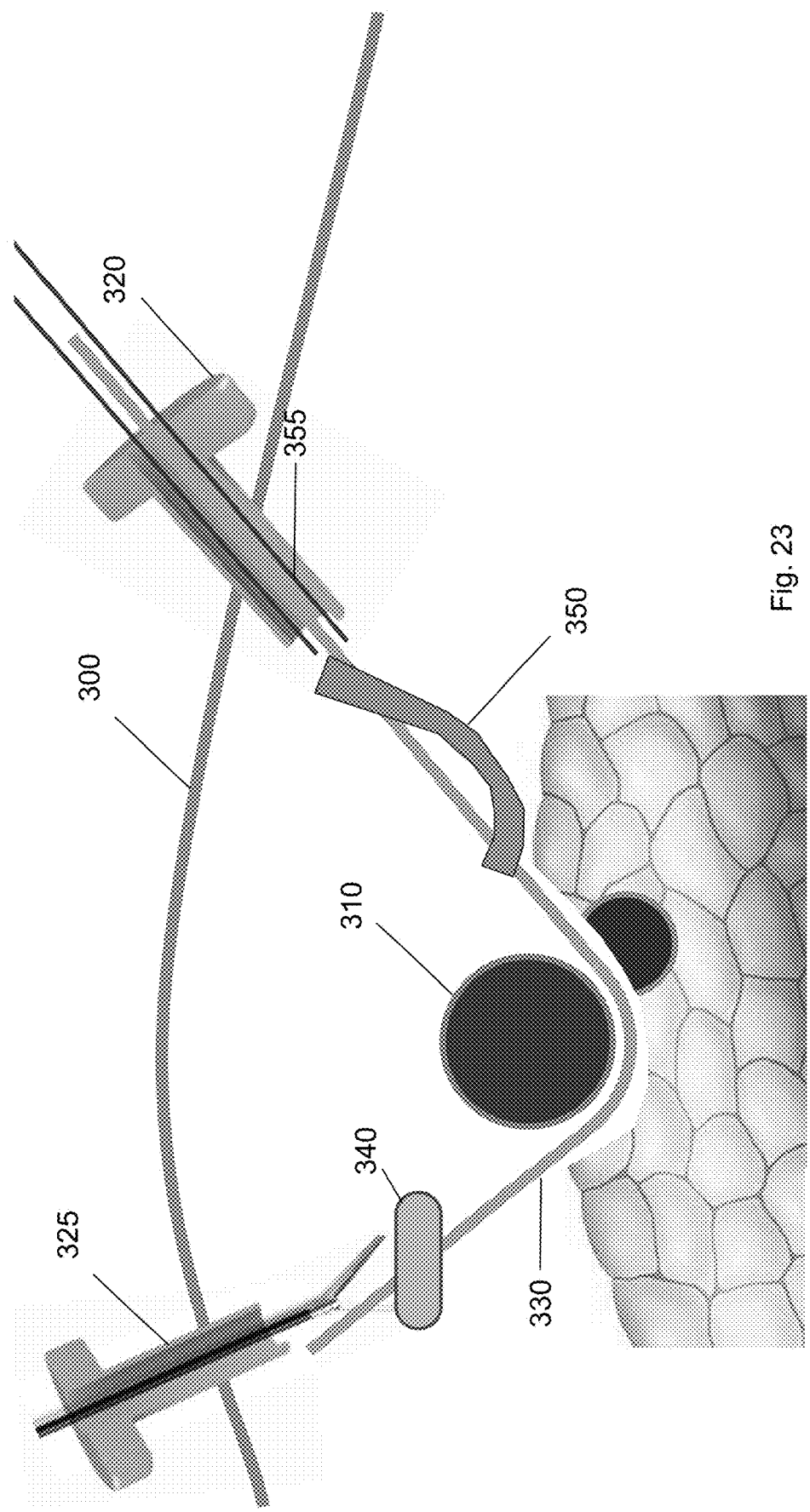
FIG. 23 shows the ramp device at a position along the guidewire according to one embodiment of the present invention.
Figure 24:
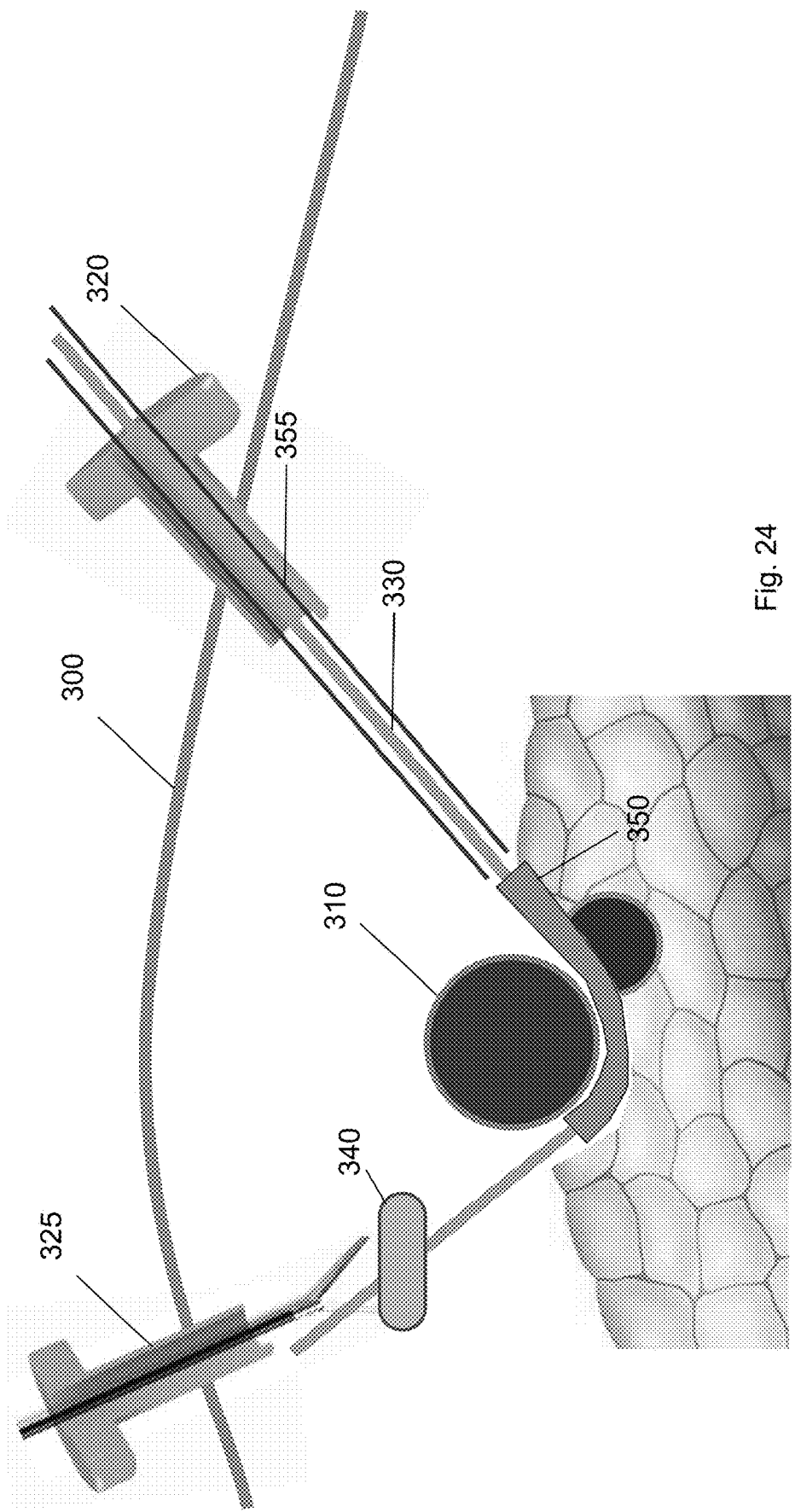
FIG. 24 shows the ramp device guided to a position underneath the target biological structure according to one embodiment of the present invention.

FIGS. 22-24 show a ramp device 350 guided over the guidewire 330 from the first trocar 320 to a position underneath the target biological structure 310 according to embodiments of the present invention. FIGS. 22 and 23 show the ramp device 350 inserted over the guidewire 330 through the first trocar 320 to a position along the guidewire. The ramp device 350 may include a rear face having a conduit for receiving the guidewire. Ultimately, the ramp device 350 is threaded over the guidewire 330 from the first trocar 320 to a position underneath the target biological structure 310 such that the target biological structure 310 is partly supported by the ramp device 350.

As shown in FIG. 23, the ramp device 350 is at a position along the guidewire 330. In this position, an external device, e.g., a pushing tool 355, may be inserted through the first trocar 320 to push the ramp device 350 along the guidewire 330. In some embodiments, the ramp device 350 may comprise an elastomeric material. The elastomeric material may be a flexible material that enables the ramp device 350 to deform to pass through the first trocar 320, but spring back to its original form once it passes through the first trocar 320. The ramp device 350 may have a curvature with respect to a long axis of the guidewire 330. In some embodiments, the ramp device 350 may be any one of the devices described above.

FIG. 24 shows the ramp device 350 partly beneath the target biological structure 310. In some embodiments, the ramp device 350 includes a first sidewall and a second sidewall positioned opposite to the first sidewall. The first sidewall and the second sidewall form a cavity or channel therebetween. When the ramp device 350 is positioned underneath the target biological structure 310, a part of the target biological structure 310 extends from being positioned on the first sidewall to extending over the cavity to being positioned on the second sidewall. In this way, a part of the target biological structure 310 is supported on the ramp device 350.

Figure 25:
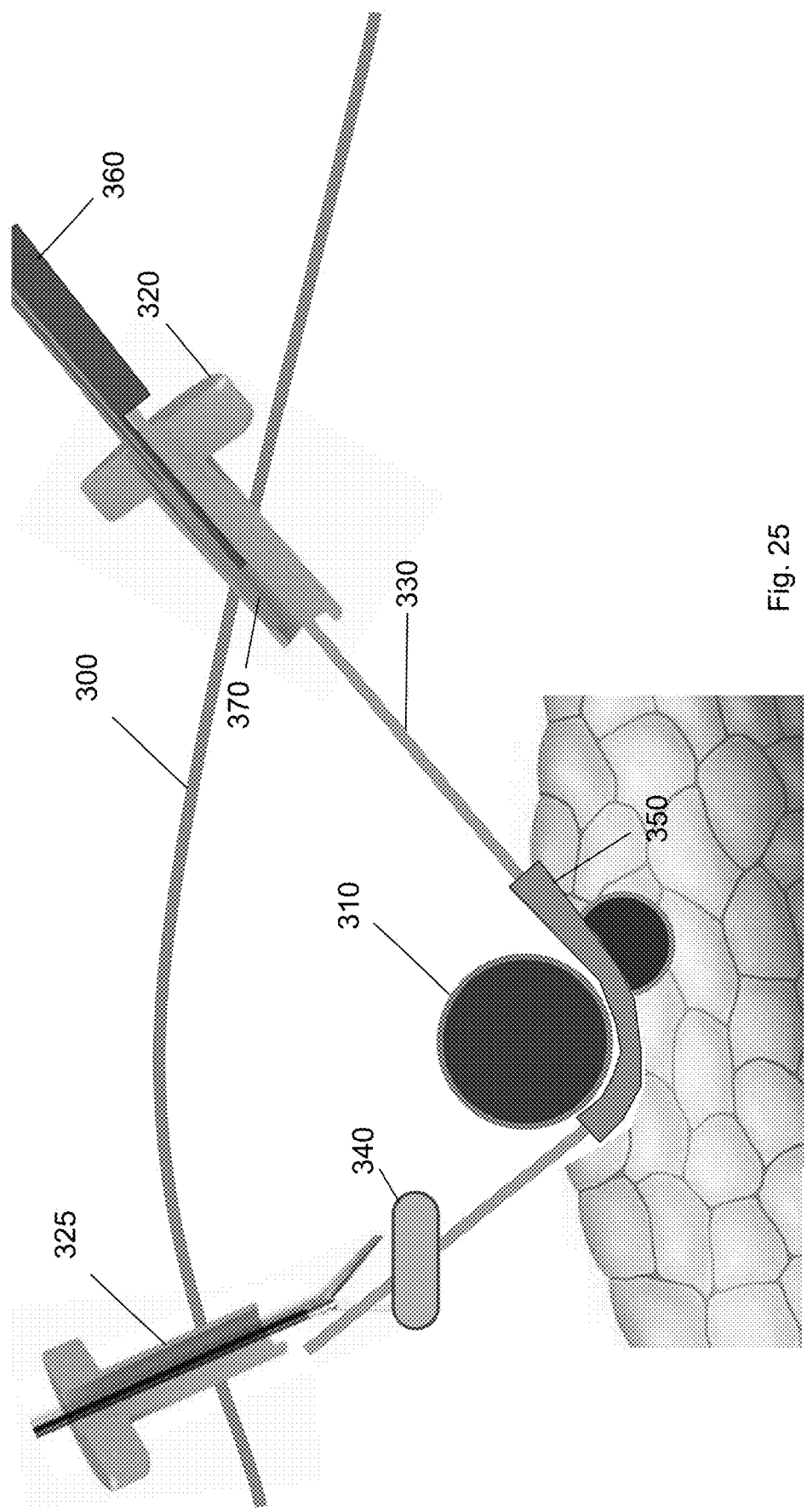
FIG. 25 shows a cuff deployment tool introduced over the guidewire through the first trocar according to one embodiment of the present invention.
Figure 26:
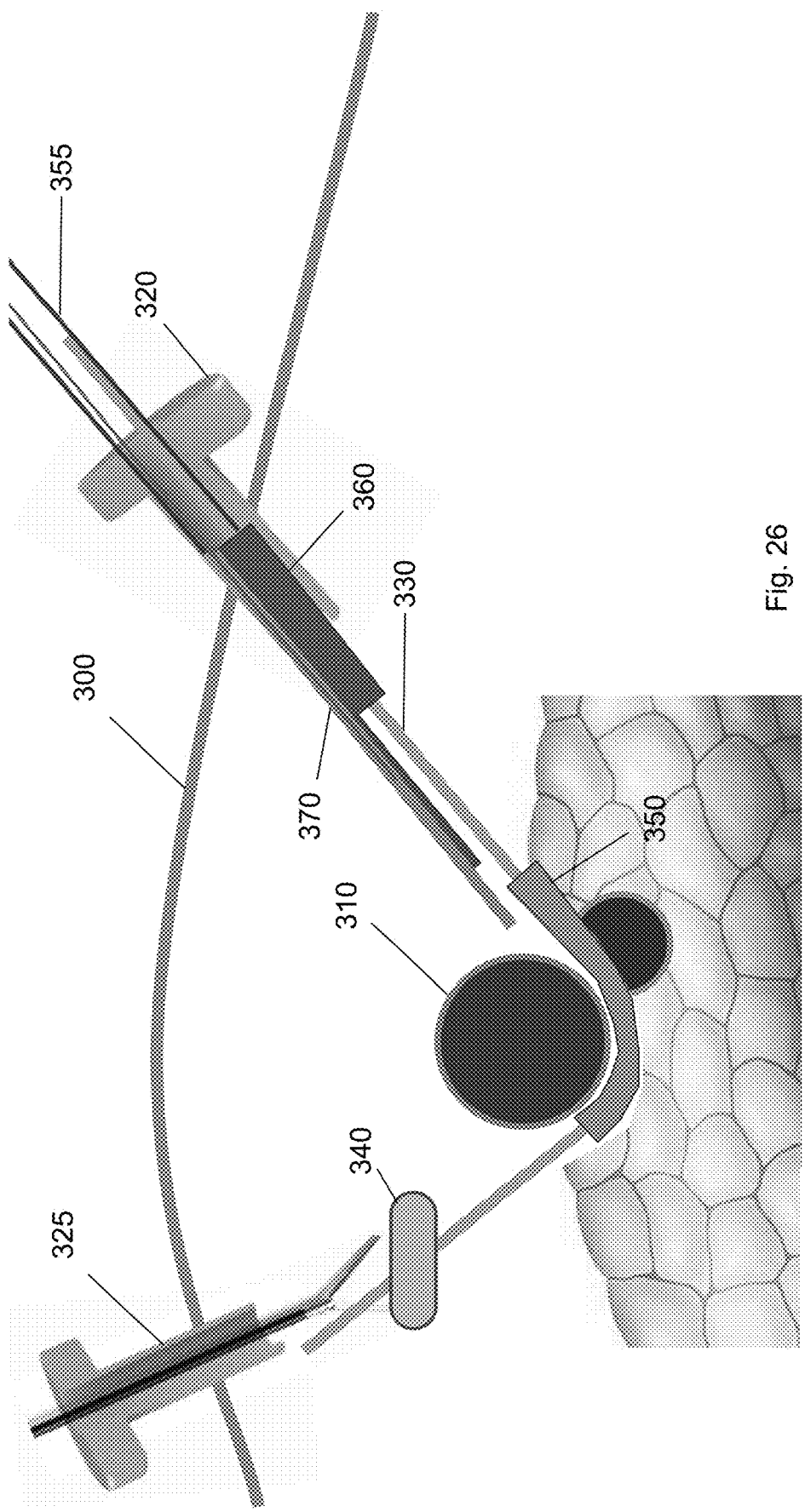
FIG. 26 shows the cuff deployment tool at a position along the guidewire according to one embodiment of the present invention.
Figure 27:
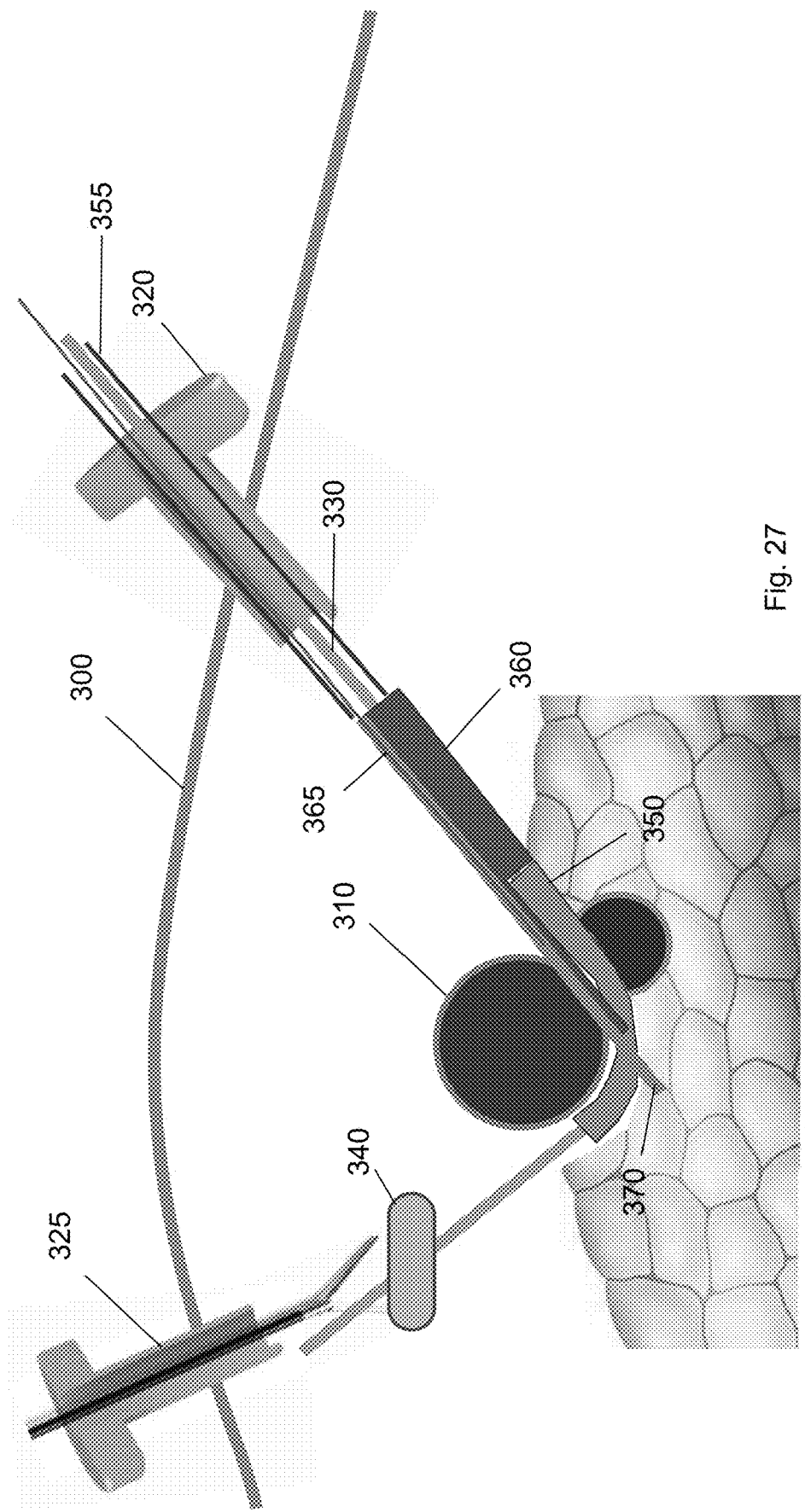
FIG. 27 shows the cuff deployment tool engaged with the ramp device at a position partly underneath the target biological structure according to one embodiment of the present invention.

FIGS. 25-27 show a cuff deployment tool 360 guided over the guidewire 330 to the target biological structure 310 according to embodiments of the present invention. FIG. 25 shows the cuff deployment tool 360 introduced over the guidewire through the first trocar 320. The cuff deployment tool 360 may include an interior volume and a cuff 370 positioned within the interior volume. The cuff 370 in the cuff deployment tool 360 may be deployed such that the cuff 370 moves from within the interior volume to an extended position. In the extended position, at least part of the cuff 370 is positioned between the ramp device 350 and the target biological structure 310.

The cuff deployment tool 360 is guided along the guidewire 330 to position underneath the target biological structure 310. For example, FIG. 26 shows the cuff deployment tool 360 at a position along the guidewire 330. In this position, an external device, e.g., a pushing tool 355, may be inserted through the first trocar 320 to push the cuff deployment tool 360 along the guidewire 330. The cuff deployment tool 360 is pushed along the guidewire 330 until it is partly underneath the target biological structure 310.

FIG. 27 shows the cuff deployment tool 360 engaged with the ramp device 350 at a position partly underneath the target biological structure 310. In this position, a portion of the cuff deployment tool 360 may extend into the channel between the sidewalls of the ramp device 350. For example, the cuff 370 within the interior volume of the cuff deployment tool 360 may extend into the channel of the ramp device 350. In this configuration, when the cuff 370 is deployed, it may move along the curvature of the ramp device 350 onto the target biological structure 310. In some embodiments, the cuff deployment tool 360 includes a retention wire 365. The retention wire 365 may be positioned in a first position when the cuff deployment tool 360 is threaded over the guidewire. In the first position, the cuff 370 is retained within the interior volume.

Figure 28:
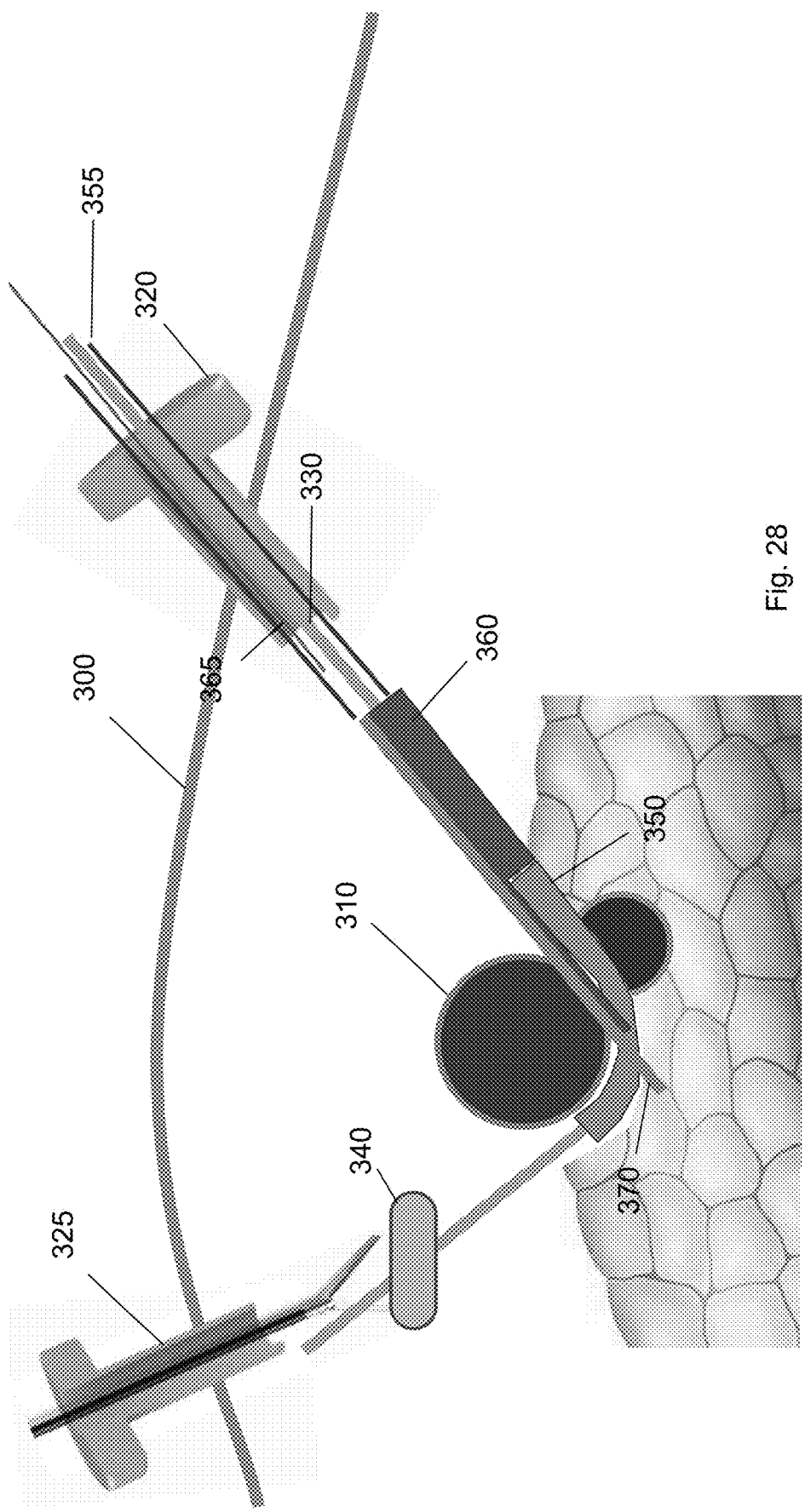
FIG. 28 shows a retention wire removed from the cuff deployment tool to deploy the cuff according to one embodiment of the present invention.
Figure 29:
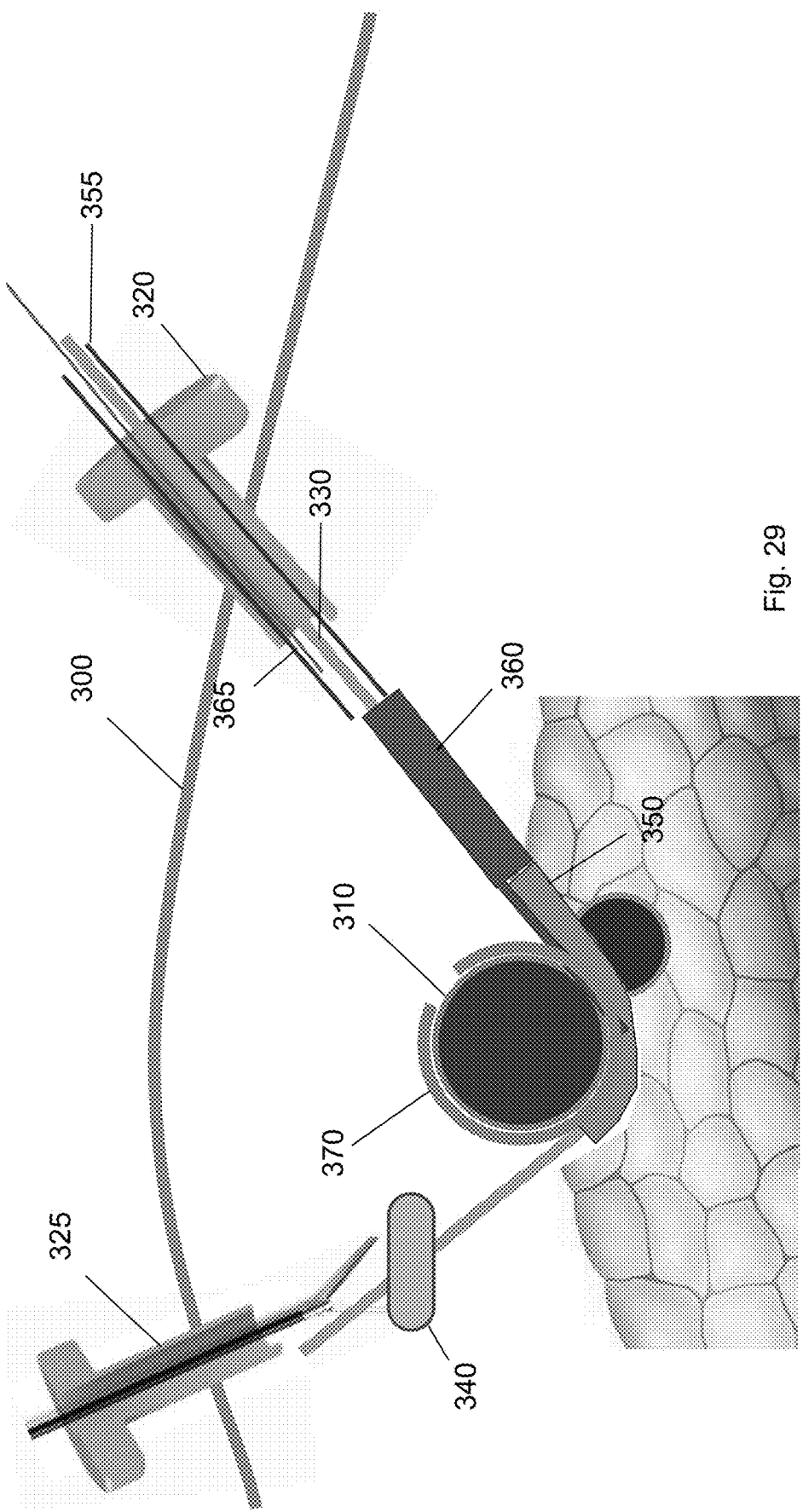
FIG. 29 shows the cuff wrapped around the target biological structure according to one embodiment of the present invention.

FIG. 28 shows a retention wire 365 removed from the cuff deployment tool 360 to deploy the cuff 370. In a second position, the cuff 370 is deployed onto the target biological structure 310. When the cuff 370 is deployed, it transitions to a deployed state. The cuff 370 may be in a helical configuration in the deployed state. As shown in FIG. 29, the cuff 370 wraps around a part of the target biological structure 310. In some embodiments, when guiding a cuff deployment tool 360 over the guidewire to the ramp device 350, the cuff deployment tool 360 contacts the end wall of the ramp device 350 to angle the cuff 370 about the target biological structure 310.

Figure 30:
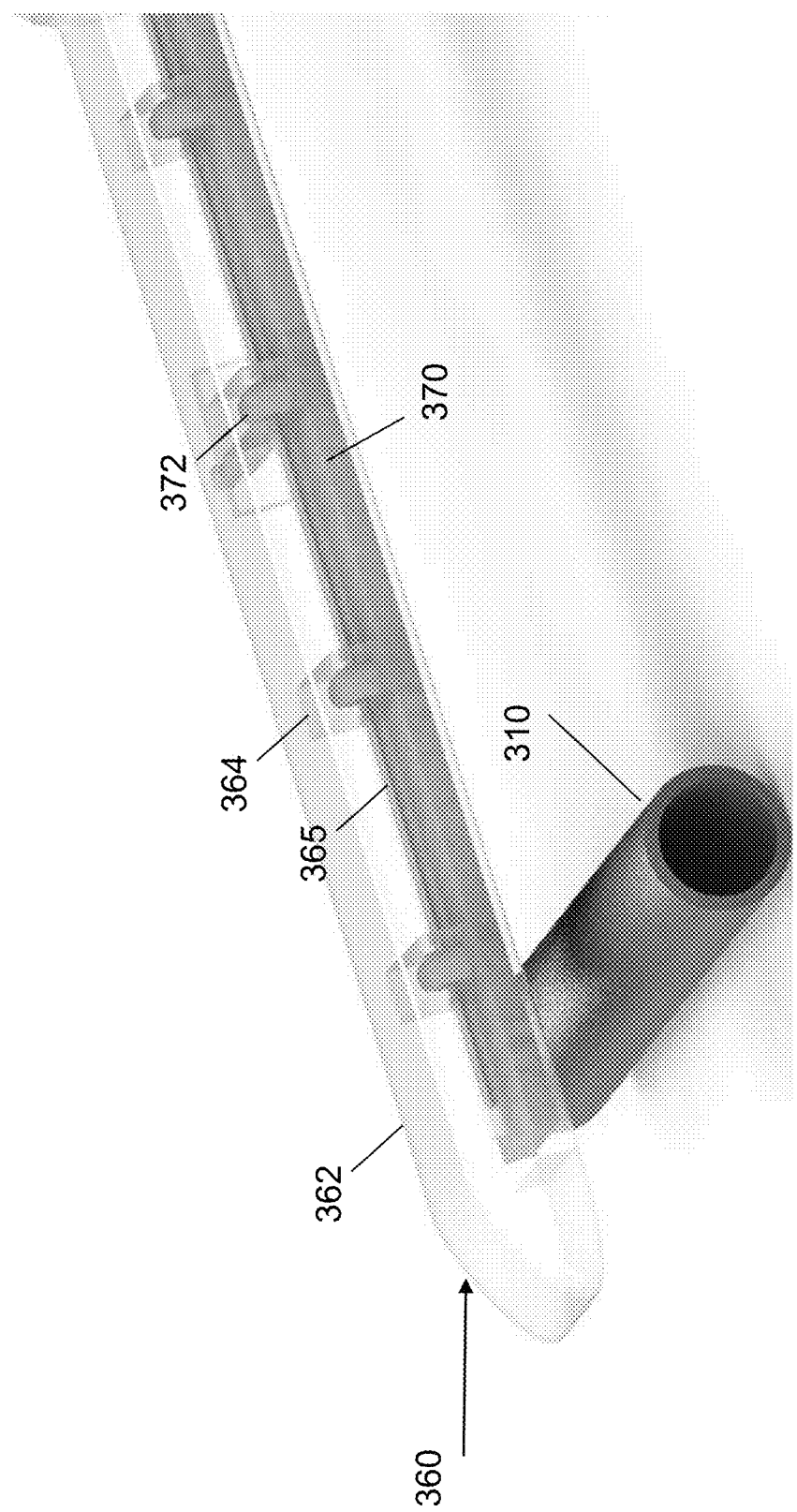
FIG. 30 shows the cuff deployment tool according to one embodiment of the present invention.

FIG. 30 shows the cuff deployment tool 360 according to one embodiment of the present invention. The cuff deployment tool 360 is configured to deliver a cuff 370 onto a target biological structure 310. The cuff deployment tool 360 may comprise a main body 362 including an interior volume for receiving a cuff 370. The main body 362 may include one or more recessed portions 364 adjacent to the interior volume. The cuff 370 may include one or more protrusions 372 that nest within the one or more recessed portions 364 of the main body 362. Each of the protrusions 372 on the cuff 370 includes an aperture. In some embodiments, the cuff 370 is a flattened helical cuff.

The cuff deployment tool 360 may further include a retention wire 365. The retention wire 365 may be threaded through the recessed portions 364 in the main body 362 and the corresponding protrusions 372 of the cuff 370 to retain the cuff 370 within the interior volume. In a first position, the cuff 370 is retained within the interior volume via the retention wire 365 in a flat configuration. In a second position, the retention wire is removed to deploy the cuff 370. In the deployed state, the cuff 370 is in a helical configuration.

Figure 31:
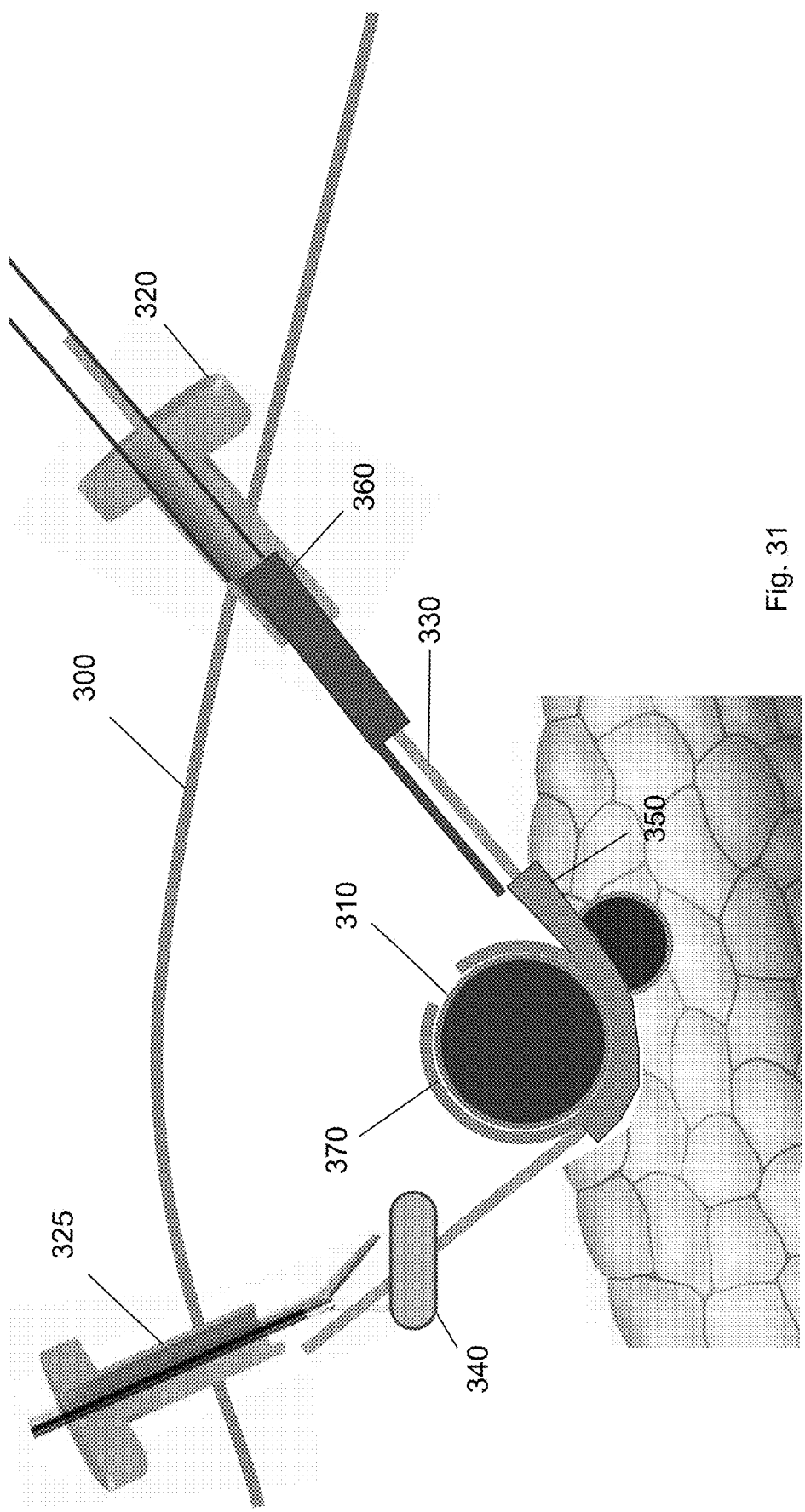
FIG. 31 shows removal of the cuff deployment tool from through the first trocar according to one embodiment of the present invention.
Figure 32:
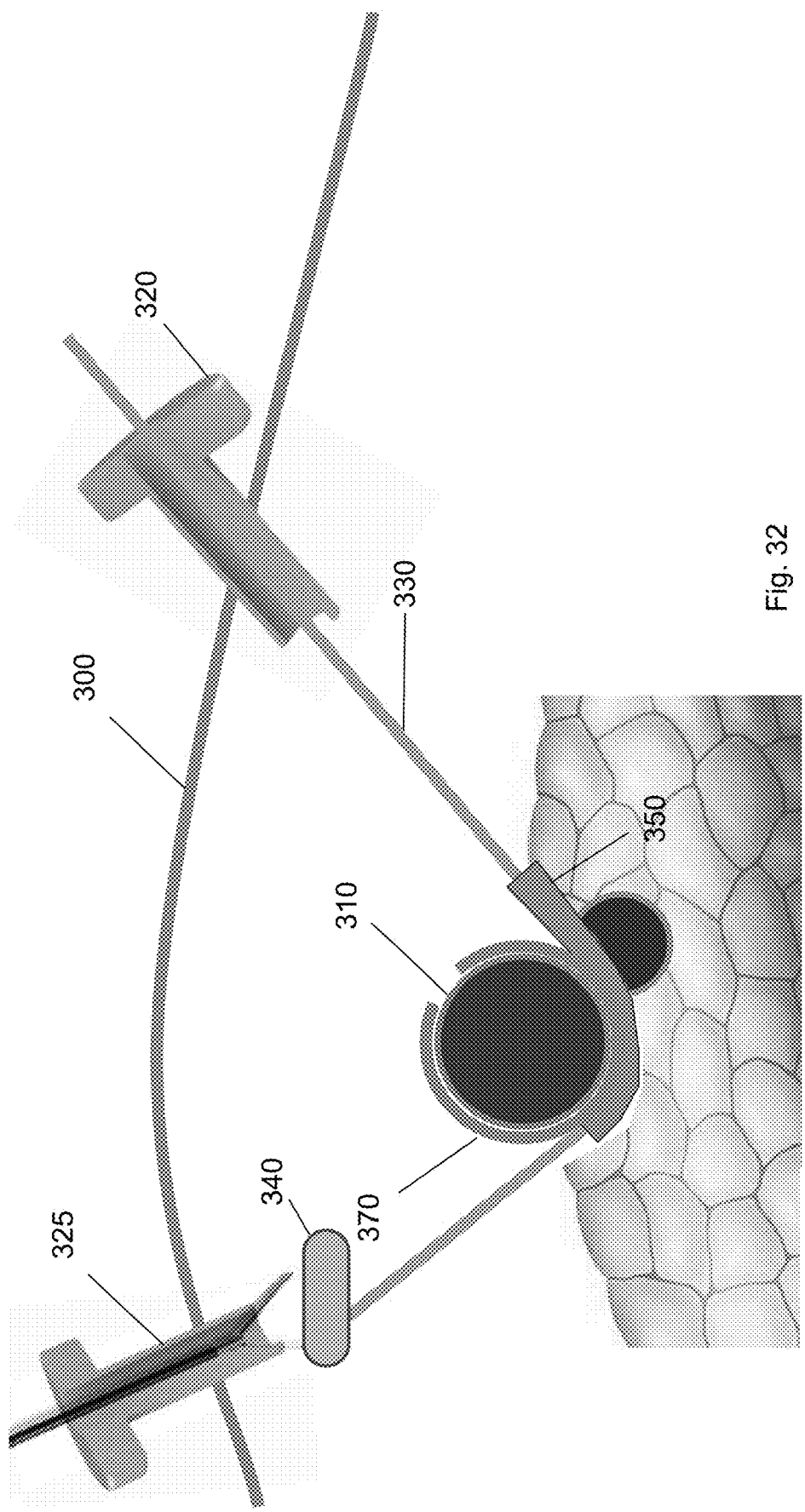
FIG. 32 shows removal of the balloon tool using a medical tool according to one embodiment of the present invention.
Figure 33:
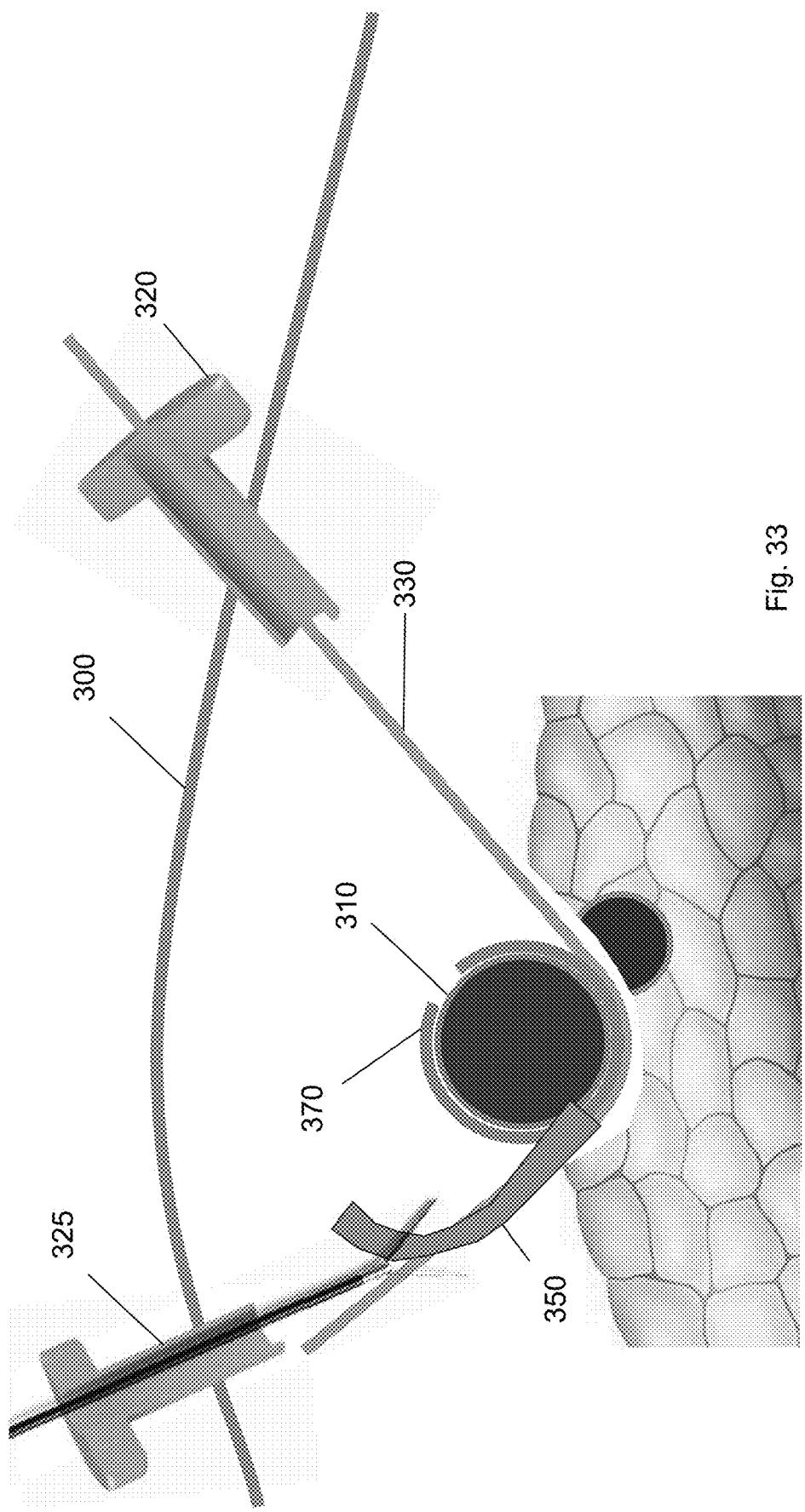
FIG. 33 shows removal of the ramp device using a medical tool according to one embodiment of the present invention.
Figure 34:
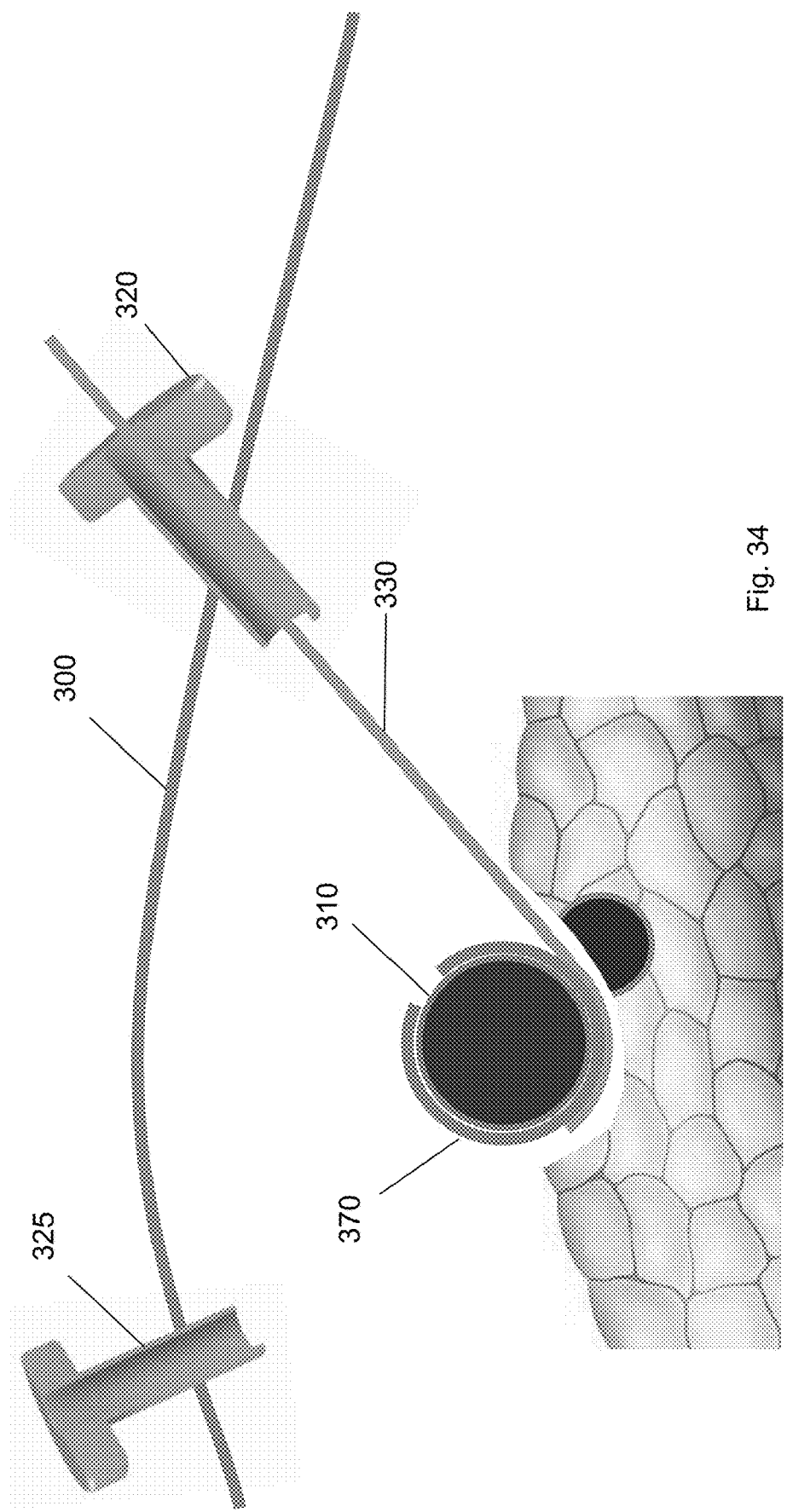
FIG. 34 shows removal of the guidewire via the first trocar according to one embodiment of the present invention.

After the cuff is deployed, each of the tools used in the method are removed from the surgical site. Specifically, as shown in FIGS. 31-34, the cuff deployment tool 360, ramp device 350, balloon tool 340, and guidewire are each removed via one of the trocars 320, 325. For example, FIG. 31 shows removal of the cuff deployment tool 360 from the surgical site through the first trocar 320. FIG. 32 shows removal of the balloon tool 340 via the second trocar 325 using a medical tool. FIG. 33 shows removal of the ramp device 350 through the second trocar 325 using a medical tool. FIG. 34 shows removal of the guidewire 330 via the first trocar 320. FIG. 35 shows the cuff around the target biological structure according to one embodiment of the present invention.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that embodiments of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art.

We claim:

1. A method comprising:
   inserting a guidewire through an incision in a patient underneath an exterior surface of a target biological structure;
   guiding a ramp device over the guidewire to a position underneath the target biological structure such that the target biological structure is partly supported by the ramp device, the ramp device having a curvature with respect to a long axis of the guidewire;
   guiding a cuff deployment tool over the guidewire to the ramp device, the cuff deployment tool comprising an interior volume and a cuff positioned within the interior volume; and
   causing the cuff from the cuff deployment tool to deploy such that the cuff moves from within the interior volume to an extended position, wherein at least part of the cuff is positioned between the ramp device and the biological structure in the extended position.

2. The method of claim 1, further comprising, prior to threading the ramp device over the guidewire:
   guiding a balloon tool over the guidewire to a position underneath the target biological structure, the balloon tool including a balloon; and
   causing the balloon to be inflated when the balloon tool is at the position underneath the target biological structure to provide pressure to the target biological structure.

3. The method of claim 2, further comprising selectively inflating and deflating the balloon at a plurality of positions along the guidewire, wherein the balloon is a hemostatic balloon.

4. The method of claim 2, further comprising deflating the balloon and removing the balloon from the patient.

5. The method of claim 1, further comprising:
   making one or more incisions in the skin of a patient;
   positioning a trocar in each of the one or more incisions.

6. The method of claim 5, wherein the one or more incisions include the incision and another incision, and wherein the method further comprises:
   inserting a grasping tool through the other incision;
   grasping an end of the guidewire with the grasping tool;
   guiding the end of the guidewire towards the other incision using the grasping tool; and
   securing the end of the guidewire at the trocar positioned in the other incision.

7. The method of claim 6, wherein inserting the guidewire through the incision includes inserting a distal end of the guidewire through the incision, and wherein the distal end of the guidewire comprises a tip having a curvature with respect to the long axis of the guidewire.

8. The method of claim 7, wherein the tip includes an atraumatic J-shaped tip.

9. The method of claim 1, wherein the ramp device further comprises:
   a first sidewall;
   a second sidewall positioned opposite to the first sidewall; and
   a cavity formed between the first sidewall and the second sidewall,
   wherein, when the ramp device is positioned underneath the target biological structure, a part of the target biological structure extends from being positioned on the first sidewall to extending over the cavity to being positioned on the second sidewall.

10. The method of claim 1, wherein the cuff deployment tool further comprises a retention wire, the retention wire being positioned in a first position when the cuff deployment tool is threaded over the guidewire, wherein the cuff is retained within the interior volume when the retention wire is in the first position, and wherein causing the cuff to deploy includes causing the retention wire to move from the first position to a second position.

11. The method of claim 10, wherein causing the cuff to deploy causes the cuff to transition to a deployed state, the cuff being in a helical configuration in the deployed state.

12. The method of claim 11, wherein causing the cuff to deploy results in the cuff wrapping around a part of the target biological structure.

13. A method comprising:
making a first incision and a second incision in the skin of a patient;
placing a first trocar in the first incision and a second trocar in the second incision;
insufflating an area underneath the skin of the patient to access a target biological structure;
guiding a guidewire through the first trocar to a position underneath a target biological structure to the second trocar, the guidewire having a proximal end and a distal end;
securing the distal end of the guidewire at the second trocar;
guiding a balloon tool over the guidewire to a position underneath the target biological structure, the balloon tool including a balloon; and
causing the balloon to be inflated when the balloon tool is at the position underneath the target biological structure to provide pressure to the target biological structure;
guiding a ramp device over the guidewire to a position underneath the target biological structure, the ramp device comprising an end wall having a curvature with respect to a long axis of the guidewire;
guiding a cuff deployment tool over the guidewire to the ramp device, wherein the cuff deployment tool having an interior volume and a cuff positioned within the interior volume; and
causing the cuff from the cuff deployment tool to deploy such that the cuff moves from within the interior volume to an extended position, wherein at least part of the cuff is positioned between the ramp device and the biological structure in the extended position.

14. The method of claim 13, wherein, when guiding the cuff deployment tool over the guidewire to the ramp device, the cuff deployment tool contacts the end wall of the ramp device to angle the cuff deployment tool about the target biological structure.

15. The method of claim 13, wherein the ramp device comprises an elastomeric material.

16. The method of claim 13, wherein the cuff deployment tool further comprises a retention wire, the retention wire being positioned in a first position when the cuff deployment tool is threaded over the guidewire, wherein the cuff is retained within the interior volume when the retention wire is in the first position, and wherein causing the cuff to deploy includes causing the retention wire to move from the first position to a second position.

17. The method of claim 16, wherein causing the cuff to deploy causes the cuff to transition to a deployed state, the cuff being in a helical configuration in the deployed state.

18. The method of claim 17, wherein causing the cuff to deploy results in the cuff wrapping around a part of the target biological structure.

19. The method of claim 13, further comprising applying a tension to the guidewire to position the target biological structure.

* * * * *